(12) United States Patent
Nilsson et al.

(10) Patent No.: US 9,353,141 B2
(45) Date of Patent: May 31, 2016

(54) GALECTOSIDE INHIBITORS OF GALECTINS

(71) Applicant: GALECTO BIOTECH AB, Copenhagen (DK)

(72) Inventors: Ulf Nilsson, Lund (SE); Hakon Leffler, Lund (SE); Balaram Mukhopadhyay, Kolkata West Bengal (IN); Vishal Rajput, Edmonton, CA (US)

(73) Assignee: Galecto Biotech AB, Copenhagen (DK)

( * ) Notice: Subject to any disclaimer, the term of this patent is extended or adjusted under 35 U.S.C. 154(b) by 0 days.

(21) Appl. No.: 14/364,169

(22) PCT Filed: Jan. 24, 2013

(86) PCT No.: PCT/EP2013/051339
§ 371 (c)(1),
(2) Date: Jun. 10, 2014

(87) PCT Pub. No.: WO2013/110704
PCT Pub. Date: Aug. 1, 2013

(65) Prior Publication Data
US 2014/0336146 A1 Nov. 13, 2014

(30) Foreign Application Priority Data
Jan. 25, 2012 (EP) .................................. 12152413

(51) Int. Cl.
*C07H 15/26* (2006.01)
*C07H 19/01* (2006.01)

(52) U.S. Cl.
CPC ................ *C07H 19/01* (2013.01); *C07H 15/26* (2013.01)

(58) Field of Classification Search
None
See application file for complete search history.

(56) References Cited

U.S. PATENT DOCUMENTS

| | | |
|---|---|---|
| 7,230,096 B2 | 6/2007 | Nilsson |
| 7,638,623 B2 | 12/2009 | Nilsson |
| 7,700,763 B2 | 4/2010 | Leffler |
| 8,697,862 B2 | 4/2014 | Nilsson |
| 8,703,720 B2 | 4/2014 | Leffler |
| 2011/0130553 A1 | 6/2011 | Nilsson |
| 2012/0165277 A1 | 6/2012 | Leffler |
| 2014/0011765 A1 | 1/2014 | Nilsson |
| 2014/0171630 A1 | 6/2014 | Nilsson |
| 2014/0200190 A1 | 7/2014 | Leffler |

FOREIGN PATENT DOCUMENTS

| | | |
|---|---|---|
| WO | 2005113568 | 12/2005 |
| WO | 2005113569 | 12/2005 |
| WO | WO2005/113568 | * 12/2005 |
| WO | 2010126435 | 11/2010 |
| WO | 2014067986 | 5/2014 |

OTHER PUBLICATIONS

Cumpstey et al (2007). "Studies of arginine-arene interactions through synthesis and evaluation of a series of Galectin-Binding Aromatic Lactose Esters". ChemBioChem 8:1389-1398.
Saegusa et al. (2009). "Galectin-3 is critical for the development of the allergic inflammatory response in a mouse model of atopic dermatitis". Am J Pathol 174: 922-931.
Van Hattum et al. (2013). "Tuning the Preference of Thiodigalactoside- and Lactosamine-Based Ligands to Galectin-3 over Galectin-1". J. Med. Chem. 56: 1350-1354.
Van Scherpenzeel et al. (2009). "Synthesis and Evaluation of New Thiodigalactoside-Based Chemical Probes to Label Galectin-3". ChemBioChem 10: 1724-1733.
Volarevic et al (2012). "Galectin-3 Deficiency Prevents Concanavalin A-Induced Hepatitis in Mice". Hepatology 55:1954-1964.
Voss et al (2012). "Inhibition of Cell-Free Splicing by Saccharides That Bind Galectins and SR Proteins". Journal of Carbohydrate Chemistry 31: 519-534.
Vrasidas et al (2003). "Rigidified multivalent lactose molecules and their interactions with mammalian galectins: a route to selective inhibitors". Org. Biomol. Chem. 1:803-810.

(Continued)

*Primary Examiner* — Traviss C McIntosh, III
(74) *Attorney, Agent, or Firm* — Cheryl H. Agris; Agris & von Natzmer, LLP

(57) ABSTRACT

The present invention relates to novel compounds prepared from readily accessible 3-O-propargyl-D-galactopyranoside derivatives and having an effect as i.a., galectin inhibitors, the use of said compounds as a medicament as well as for the manufacture of a medicament for treatment of disorders relating to the binding of galectin to ligands in a mammal, wherein said galectin is preferably a galectin-3. The novel compounds are defined by the general formula (I).

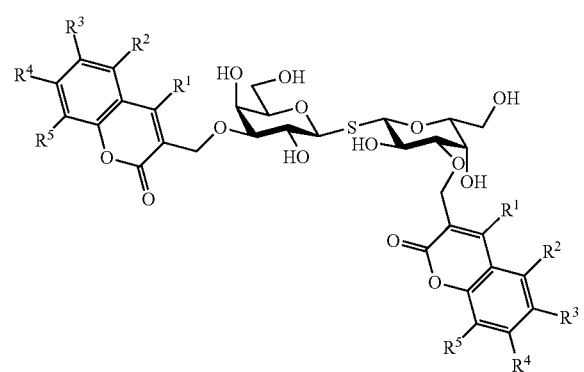

(I)

19 Claims, No Drawings

(56) References Cited

OTHER PUBLICATIONS

Wang et al (2013). "Design and synthesis of glycoprotein-based multivalent glyco-ligands for influenza hemagglutinin and human galectin-3". Bioorganic & Medicinal Chemistry 21:2037-2044.
Yang et al (2012). "Synthesis of multivalent N-acetyl lactosamine modified quantum dots for the study of carbohydrate and galectin-3 interactions". Tetrahedron 68:7148-7154.
Zou et al (2005). "Peptides specific to the galectin-3 carbohydrate recognition domain inhibit metastasis-associated cancer cell adhesion". Carcinogensis 26(2):309-318.
US Office Action dated Aug. 29, 2014 for U.S. Appl. No. 13/832,672.
International Preliminary Report on Patentability for PCT/EP2013/051339, dated Jul. 29, 2104.
International Search Report and Written Opinion for PCT/EP2013/051339, dated Feb. 28, 2013.
Almkvist et al. (2001) "Lipopolysaccharide-induced gelatinase granule mobilization primes neutrophils for activation by galectin-3 and f-Met-Leu-Phe". Infect. Immun. 69: 832-837.
André et al. (2012). "Synthesis of bivalent lactosides and their activity as sensors for differences between lectins in inter- and intrafamily comparisons". Bioorganic & Medicinal Chemistry Letters 22: 313-318.
André et al. (2010). "Glycocluster Design for Improved Avidity and Selectivity in Blocking Human Lectin/Plant Toxin Binding to Glycoproteins and Cells". Molecular Pharmaceutics 7: 2270-2279.
André et al. (2009). "Carbamate-Linked Lactose: Design of Clusters and Evidence for Selectivity to Block Binding of Human Lectins to (Neo)Glycoproteins with Increasing Degree of Branching and to Tumor Cells". Bioconjugate Chem. 20: 1716-1728.
André et al. (2008). "Calix[n]arene-Based Glycoclusters: Bioactivity of Thiourea-Linked Galactose/Lactose Moieties as Inhibitors of Binding of Medically Relevant Lectins to a Glycoprotein and Cell-Surface Glycoconjugates and Selectivity among Human Adhesion/Growth—Regulatory Galectins". ChemBioChem 9: 1649-1661.
André et al (2007). "Discovery of galectin ligands in fully randomized combinatorial one-bead-one-compound (glyco) peptide libraries". Bioorganic & Medicinal Chemistry Letters 17: 793-798.
Andre et al. (2006). "Glycosyldisulfides from dynamic combinatorial libraries as O-glycoside mimetics for plant and endogenous lectins: Their reactivities in solid-phase and cell assays and conformational analysis by molecular dynamics simulations". Bioorganic & Medicinal Chemistry 14: 6314-6326.
André et al. (2005). "Identification of peptide ligands for malignancy- and growth-regulating galectins using random phage-display and designed combinatorial peptide libraries". Bioorganic & Medicinal Chemistry 13: 563-573.
Andre et al. (2004). "Persubstituted Cyclodextrin-Based Glycoclusters as Inhibitors of Protein-Carbohydrate Recognition Using Purified Plant and Mammalian Lectins and Wild-Type and Lectin-Gene-Transfected Tumor Cells as Targets". Bioconjugate Chem. 15: 87-98.
Andre et al (2003). "First demonstration of differential inhibition of lectin binding by synthetic tri- and tetravalent glycoclusters from cross-coupling of rigidified 2-propynyl lactoside". Org. Biomol. Chem. 1: 3909-3916.
Andre et al. (2001). "Wedgelike Glycodendrimers as Inhibitors of Binding of Mammalian Galectins to Glycoproteins, Lactose Maxiclusters, and Cell Surface Glycoconjugates". ChemBioChem 2: 822-830.
Andre et al. (1999). "Lactose-containing starburst dendrimers: influence of dendrimer generation and binding-site orientation of receptors (plant/animal lectins and immunoglobulins) on binding properties". Glycobiology 9: 1253-1261.
Arnusch et al. (2004). "Interference of the galactose-dependent binding of lectins by novel pentapeptide ligands". Bioorganic & Medicinal Chemistry 14:1437-1440.
Arsenijevic et al. (2012). "The role of Galectin 3 in Con A induced liver injury". Immunology 137:311.

Ballell et al. (2006). "A new chemical probe for the detection of the cancer-linked galectin-3". Org. Biomol. Chem. 4: 4387-4394.
Barondes et al. (1994). Galectins. Structure and function of a large family of animal lectins. J. Biol. Chem. 269: 20807-20810.
Bartoloni et al. (2013). "Targeting Matrix Metalloproteinases: Design of a Bifunctional Inhibitor for Presentation by Tumour-Associated Galectins". Chemistry—A European Journal 19: 1896-1902.
Belitsky et al. (2007). "Multivalent Interactions between Lectins and Supramolecular Complexes: Galectin-1 and Self-Assembled Pseudopolyrotaxanes". Chemistry & Biology 14: 1140-1151.
Blois et al. (2007). "A pivotal role for galectin-1 in fetomaternal tolerance". Nat Med 13: 1450-1457.
Bum-Erdene et al. (2013). "Investigation into the Feasibility of Thioditaloside as a Novel Scaffold for Galectin-3-Specific Inhibitors". ChemBioChem 14:1331-1342.
Chen et al. (2012). "Targeting Galectin-1 and Galectin-3 Attenuates VEGF-A-induced Angiogenesis". Mol. Biol. Cell (suppl), Abstract No. 3215.
Chen et al. (2013). "TDX, a galectin-1 and galectin-3-specific inhibitor mitigates VEGF-A-induced angiogenesis" FASEB J 27: 828.1.
Collins et al. (2012). "Taloside Inhibitors of Galectin-1 and Galectin-3". Chem. Biol. Drug Des. 79:339-346.
Cumpstey et al. (2005). "Synthesis of a phenyl thio-β-D-galactopyranoside library from 1,5-difluoro-2,4-dinitrobenzene: discovery of efficient and selective monosaccharide inhibitors of galectin-7". Org. Biomol. Chem. 3: 1922-1932.
Cumpstey et al. (2005). "C2-Symmetrical thiodigalactoside bis-benzamido derivatives as high-affinity inhibitors of galectin-3: Efficient lectin inhibition through double arginine-arene interactions". Angew. Chem. Int. Ed. 44: 5110-5112.
Cumpstey et al. (2008). "Double affinity amplification of galectin-ligand interactions through arginine-arene interactions: Synthetic, thermodynamic, and computational studies with aromatic diamido-thiodigalactosides". Chem. Eur. J. 14: 4233-4245.
Dam et al. (2008). "Effects of clustered epitopes in multivalent ligand-receptor interactions". Biochemistry 47: 8470-8476.
David (2004). "Design of a multivalent galactoside ligand for selective targeting of HPMA copolymer—doxorubicin conjugates to human colon cancer cells". European Journal of Cancer 40: 148-157.
Delacour et al. (2007). "Apical Sorting by Galectin-3-Dependent Glycoprotein Clustering". Traffic 8: 379-388.
Delaine et al. (2008). Galectin-Inhibitory Thiodigalactoside Ester Derivatives Have Anti-Migratory Effects in Cultured Lung and Prostate Cancer Cells:. J Med Chem 51: 8109-8114.
Demotte et al. (2010). "A Galectin-3 Ligand Corrects the Impaired Function of Human CD4 and CD8 Tumor-Infiltrating Lymphocytes and Favors Tumor Rejection in Mice". Cancer Res. 70:7476-7488.
Dings et al. (2013). "Structure-Based Optimization of Angiostatic Agent 6DBF7, an Allosteric Antagonist of Galectin-1". J. Pharmacol. Exp. Ther. 344 589-599.
Dings et al. (2012). "Antitumor Agent Calixarene 0118 Targets Human Galectin-1 as an Allosteric Inhibitor of Carbohydrate Binding". J. Med. Chem. 55:5121-5129.
Dings et al. (2010). "Inhibiting Tumor Growth by Targeting Tumor Vasculature with Galectin-1 Antagonist Anginex Conjugated to the Cytotoxic Acylfulvene, 6-Hydroxylpropylacylfulvene". Bioconjugate Chem. 21:20-27.
Dings et al. (2008). "Ovarian tumor growth regression using a combination of vascular targeting agents anginex or topomimetic 0118 and the chemotherapeutic irofulven". Cancer Letters 265: 270-280.
Dings et al .(2003). "Anti-tumor activity of the novel angiogenesis inhibitor anginex". Cancer Letters 194:55-66.
Disney et al. (2007). "Supra molecular Recognition of Galectin 1". Chemistry & Biology 14: 1095-1097.
Fort et al. (2006). "Screening for Galectin-3 ilnhibitors from Synthetic Lacto-N-biose Libraries Using Microscale Affinity Chromatography Coupled to Mass Spectrometry". J. Org. Chem. 71: 7146-7154.
Garner et al. (2008). "Galectin-glycan lattices regulate cell-surface glycoprotein organization and signalling". Biochem Soc Trans 36: 1472-1477.

(56) References Cited

OTHER PUBLICATIONS

Giguere et al. (2011). "Inhibitory potential of chemical substitutions at bioinspired sites of β-D-galactopyranose on neoglycoprotein/cell surface binding of two classes of medically relevant lectins". Bioorg. Med. Chem. 19:3280-3287.

Giguere et al. (2008). "Synthesis of stable and selective inhibitors of human galectins-1 and -3". Bioorg. Med. Chem., 16:7811-7823.

Giguere et al. (2006). "Carbohydrate triazoles and isoxazoles as inhibitors of galectins-1 and -3". Chem Commun: 2379-2381.

Giguere et al (2006). "Aryl O- and S-galactosides and lactosides as specific inhibitors of human galectins-1 and -3: Role of electrostatic potential at O-3". Bioorg. Med. Chem. 16:1668-1672.

Glinksy et al (1996). "Inhibition of Human Breast Cancer Metastasis in Nude Mice by Synthetic Glycoamines". Cancer Res. 56:5319-5324.

Glinsky et al. (2009). "Synthetic Galectin-3 Inhibitor Increases Metastatic Cancer Cell Sensitivity to Taxol-Induced Apoptosis In Vitro and In Vivo". Neoplasia 11; 901-909.

Gouin et al (2010). "Multimeric Lactoside "Click Clusters" as Tools to Investigate the Effect of Linker Length in Specific Interactions with Peanut Lectin, Galectin-1, and -3". ChemBioChem 11:1430-1442.

Guha et al (2013). "Cod glycopeptide with picomolar affinity to galectin-3 suppresses T-cell apoptosis and prostate cancer metastasis". Proc. Natl. Acad. Sci. 110: 5052-5057.

Huflejt et al. (2004). "Galectin-4 in normal tissues and cancer". Glycoconj. J. 20: 247-255.

Ingrassia et al. (2006). "A Lactosylated Steroid Contributes in Vivo Therapeutic Benefits in Experimental Models of Mouse Lymphoma and Human Glioblastoma." J. Med. Chem. 49: 1800-1807.

John et al. (2003) Truncated Galectin-3 Inhibits Tumor Growth and Metastasis in Orthotopic Nude Mouse Model of Human Breast Cancer. Clin. Cancer Res. 9: 2374-2383.

Kahsai et al. (2008) "Analogs of Tetrahydroisoquinoline Natural Products That Inhibit Cell Migration and Target Galectin-3 Outside of Its Carbohydrate-binding Site", J.Biol. Chem. 283:24534-24545.

Lau et al. (2008). "N-Glycans in cancer progression". Glycobiology 18: 750-760.

Lau et al. (2007). "Complex N-glycan number and degree of branching cooperate to regulate cell proliferation and differentiation". Cell 129: 123-134.

Leffler et al. (1986) "Specificity of binding of three soluble rat lung lectins to substituted and unsubstituted mammalian beta-galactosides". J. Biol. Chem. 261:10119-10126.

Leffler "Galectins Structure and Function—A Synopsis in Mammalian Carbohydrate Recognition Systems" (Crocker, P. ed.) Springer Verlag, Heidelberg, 2001 pp. 57-83.

Leffler et al. (2004). "Introduction to galectins". Glycoconj. J. 19: 433-440.

Leyden et al. (2009). "Synthesis of Bivalent Lactosides Based on Terephthalamide, N, N'-Diglucosylterephthalamide, and Glycophane Scaffolds and Assessment of Their Inhibitory Capacity on Medically Relevant Lectins". J. Org. Chem. 74: 9010-9026.

Lin et al. (2009). "Galectin-3 Targeted Therapy with a Small Molecule Inhibitor Activates Apoptosis and Enhances Both Chemosensitivity and Radiosensitivity in Papillary Thyroid Cancer". Mol Cancer Res 7: 1655-1662.

MacKinnon et al. (2008). "Regulation of alternative macrophage activation by Galectin-3". J. Immun. 180; 2650-2658.

MacKinnon et al. (2012). "Regulation of TGF-β1 driven lung fibrosis by Galectin-3". Am. J. Resp. Crit. Care Med. 185:537-546.

Maljaars et al (2008). "Assessing the inhibitory potency of galectin ligands identified from combinatorial (glyco) peptide libraries using surface plasmon resonance spectroscopy". Analytical Biochemistry 378:190-196.

Massa et al. (1993). "L-29, an endogenous lectin, binds to glycoconjugate ligands with positive cooperativity". Biochemistry 32: 260-267.

Moise et al. (2011). "Toward Bioinspired Galectin Mimetics: Identification of Ligand-Contacting Peptides by Proteolytic-Excision Mass Spectrometry". J Amer Chem Soc 133:14844-14847.

Mossine et al. (1994). "The preparation and characterization of some Amadori compounds (I-amino-I-deoxy-D-fructose derivatives) derived from a series of aliphatic w-amino acids". Carbohydrate Research 262:257-270.

Murakami et al. (2011). "Synthesis and galectin-binding activities of mercaptododecyl glycosides containing a terminal β-galactosyl group". Bioorganic & Medicinal Chemistry Letters 21: 1265-1269.

Nangia-Makker et al. (2002). "Inhibition of Human Cancer Cell Growth and Metastasis in Nude Mice by Oral Intake of Modified Citrus Pectin". Journal of the National Cancer Institute 94: 1854-1862.

Nelson et al. (2004). "A Self-Assembled Multivalent Pseudopolyrotaxane for Binding Galectin-1". J Amer Chem Soc 126: 11914-11922.

Nishi et al. (2007). "Role of Galectin-3 in Human Pulmonary Fibrosis". Allergology Internatinal. 56:57-65.

Oberg et al. (2011). "Arene-Anion Based Arginine-Binding Motif on a Galactose Scaffold: Structure-Activity Relationships of Interactions with Arginine-Rich Galectins". Chem. Eur. J. 17:8139-8144.

Oberg et al. (2011). "Synthesis of 3-amido-3-deoxy-β-D-talopyranosides: all-cis-substituted pyranosides as lectin inhibitors". Tetrahedron 67:9164-9172.

Oberg et al. (2010). "Copper-Free Huisgen 1,3-Dipolar Cycloaddition to 3-Benzotriazolo-3-Deoxy-β-D-Galactopyranoside—Cyclization of a Galactopyranoside Azide and Benzyne". Trends in Carbohydrate Research 2:1-4.

Oberg et al. (2008). "Arginine Binding Motifs: Design and Synthesis of Galactose-Derived Arginine Tweezers as Galectin-3 Inhibitors". J. Med. Chem. 51:2297-2301.

Oberg et al. (2008). "Protein subtype-targeting through ligand epimerization: Talose-selectivity of galectin-4 and galectin-8". Bioorganic & Medicinal Chemistry Letters 18:3691-3694.

Partridge et al. (2004). "Regulation of cytokine receptors by Golgi N-glycan processing and endocytosis". Science 306: 120-124.

Perone et al. (2009). "Suppression of autoimmune diabetes by soluble galectin-1". J Immunol 182: 2641-2653.

Pienta et al. (1995). "Inhibition of spontaneous metastasis in a rat prostate cancer model by oral administration of modified citrus pectin". J Natl Cancer Inst 87, 348-353.

Platt et al. (1992). "Modulation of the Lung Colonization of B16-F1 Melanoma Cells by Citrus Pectin". J Natl Cancer Inst. 84:439-442.

Pohl et al. (1999). "Scope of Multivalent Ligand Function: Lactose-Bearing Neoglycopolymers by Ring-Opening Metathesis Polymerization". Synthesis SI:1515-1519.

Rabinovich et al. (2006). "Synthetic lactulose amines: novel class of anticancer agents that induce tumor-cell apoptosis and inhibit galectin-mediated homotypic cell aggregation and endothelial cell morphogenesis". Glycobiology 16:210-220.

Saksida et al (2012). "Galectin-3 Deficiency Protects Pancreatic Islet Cells from Cytokine-Triggered Apoptosis in Vitro". Journal of Cellular Physiology 228:1568-1576.

Salameh et al. (2005). "3-(1,2,3-Triazol-1-yl)-1-thio-galactosides as small, efficient, and hydrolytically stable inhibitors of galectin-3". Bioorganic & Medicinal Chemistry 15:3344-3346.

Salameh et al. (2006). "Thioureido N-acetyllactosamine derivatives as potent galectin-7 and 9N inhibitors". Bioorganic and Medicinal Chemistry 14:1215-1220.

Salameh et al. (2010). "1H-1,2,3-Triazol-1-yl thiodigalactoside derivatives as high affinity galectin-3 inhibitors". Bioorg Med Chem 18: 5367-5378.

Salomonsson et al. (2010). "Monovalent interactions of galectin-1". Biochemistry 49: 9518-9532.

Soomro et al (2011). "CuAAC synthesis of resorcin[4]arene-based glycoclusters as multivalent ligands of lectins". Org. Biomolec. Chem. 9:6587-6597.

Sörme et al. (2002). "Low micromolar inhibitors of galectin-3 based on 3'-derivatization of N-acetyllactosamine". ChemBioChem 3:183-189.

Sörme et al. (2003a). "Fluorescence polarization to study galectin-ligand interactions". Meth. Enzymol.362: 504-512.

(56) References Cited

OTHER PUBLICATIONS

Sörme et al. (2003b) Design and synthesis of galectin inhibitors. Meth. Enzymol.363: 157-169.

Sörme et al. (2004). "Fluorescence polarization as an analytical tool to evaluate galectin-ligand interactions". Anal. Biochem. 334: 36-47.

Sorme et al. (2005). "Structural and thermodynamic studies on cation-Π interactions in lectin-ligand Complexes: High-Affinity Galectin-3 Inhibitors through Fine-Tuning of an Arginine-Arene Interaction". J Amer Chem Soc 127:1737-1743.

St-Pierre et al. (2011). "Galectin-1-Specific Inhibitors as a New Class of Compounds to Treat HIV-1 Infection". Antimicrobial Agents and Chemotherapy 56:154-162.

Tejler et al. (2009). "Fragment-based development of triazole-substituted O-galactosyl aldoximes with fragment-induced affinity and selectivity for galectin-3". Organic and Biomolecular Chemistry 7:3982-3990.

Tejler et al. (2007). "Synthesis of galactose-mimicking 1H-(1,2,3-triazol-1-yl)-mannosides as selective galectin-3 and 9N inhibitors". Carbohydrate Research 342:1869-1875.

Tejler et al. (2006). "Synthesis of multivalent lactose derivatives by 1,3-dipolar cycloadditions: selective galectin-1 inhibition". Carbohydrate Research 341:1353-1362.

Tejler et al .(2005). "Synthesis of O-galactosyl aldoximes as potent LacNAc-mimetic galectin-3 inhibitors". Bioorganic and Medicinal Chemistry Letters 15:2343-2345.

Thijssen et al (2006). "Galectin-1 is essential in tumor angiogenesis and is a target for antiangiogenesis therapy". Proc. Natl. Acad. Sci USA 103:15975-15980.

Thijssen et al. (2007). "Galectins in the tumor endothelium: opportunities for combined cancer therapy". Blood 110: 2819-2827.

Toscano et al. (2007). "Differential glycosylation of TH1, TH2 and TH-17 effector cells selectively regulates susceptibility to cell death". Nat Immunol 8: 825-834.

Chua et al. (2005). "Pulmonary Fibrosis". Am J Respir Cell Mol Biol 33: 9-13.

Moeller et al. (2008). "The bleomycin animal model: a useful tool to investigate treatment options for idiopathic pulmonary fibrosis?". Int J Biochem Cell Biol. 40: 362-382.

Response to 2nd Written Opinion for PCT/EP2013/072691, dated Nov. 25, 2015.

IPRP for PCT/EP2013/072691, dated Jan. 26, 2015.

2nd Written Opinion for PCT/EP2013/072691, dated Oct. 20, 2014.

Response to 1st Written Opinion for PCT/EP2013/072691, dated Jul. 15, 2014.

1st Written Opinion for PCT/EP2013/07269, dated Jan. 20, 2014.

International search report for PCT/EP2013/072691, dated Jan. 2, 2014.

US Notice of Allowance dated Sep. 14, 2015 for U.S. Appl. No. 13/832,672.

US Interview Summary dated Jul. 15, 2015 for U.S. Appl. No. 13/832,672.

US Office Action dated May 21, 2015 for U.S. Appl. No. 13/832,672.

\* cited by examiner

GALECTOSIDE INHIBITORS OF GALECTINS

TECHNICAL FIELD

The present invention relates to novel compounds, the use of said compounds as medicament and for the manufacture of a medicament for the treatment of any disorder relating to the binding of a galectin to a ligand in mammals. The invention also relates to pharmaceutical compositions comprising said novel compounds.

BACKGROUND ART

Galectins are proteins with a characteristic carbohydrate recognition domain (CRD) (Barondes et al., 1994; Leffler et al., 2004). This is a tightly folded β-sandwich of about 130 amino acids (about 15 kDa) with the two defining features 1) a β-galactose binding site and 2) sufficient similarity in a sequence motif of about seven amino acids, most of which (about six residues) make up the β-galactose binding site. However, sites adjacent to the β-galactose site are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004)

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Leffler et al., 2004). These were the first discovered galectins and are abundant in many tissues.

There are now over 3500 publications on galectins in PubMed, with most, as mentioned above, about galectins-1 (>900) and -3 (>1600). Strong evidence suggests roles for galectins in e.g. inflammation and cancer, and development recently reviewed in a special issue (Leffler (editor), 2004b).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway, as yet unknown, but possibly similar to the export of e.g. IL-1 (Leffler et al., 2004). They can also function in all these compartments; for galectin-3, solid evidence published in well respected journals support roles in RNA splicing in the nucleus, inhibition of apoptosis in the cytosol, and a variety of extracellular effects on cell signaling and adhesion (Leffler (editor), 2004b). Galectin-7 and -12 also act in the cytosol by enhancing apoptosis and regulating the cell cycle and differentiation in certain cells (Hsu and Liu in Leffler (editor), 2004b). Most galectins act also extracellularly by cross-linking glycoproteins (e.g. laminin, integrins, and IgE receptors) possibly forming supramolecular ordered arrays (Brewer et al., 2002) and may thereby modulate cell adhesion and induce intracellular signals. Related to this, recent years have seen the emergence of a molecular mechanism of these galectin functions involving a formation of microdomains (lattices) within membranes, (Dam et al., 2008; Garner et al., 2008) which in turn affects intracellular trafficking and cell surface presentation of glycoprotein receptors. (Delacour et al., 2007; Lau et al., 2007; Lau et al. 2008) This has been documented in cell culture, in null mutant mice, (Blois et al., 2007; Gedronneau et al., 2008; Thijssen et al., 2007; Toscano et al., 2007; Saegusa et al., 2009) and animals treated with galectin (Blois et al., 2007; Perone et al., 2009) or galectin inhibitors. (John et al., 2003; Pienta et al., 1995; Glinsky et al., 1996)

Potential Therapeutic Use of Galectin-3 Inhibitors

Galectin-3 has been implicated in diverse phenomena and, hence, inhibitors may have multiple uses. It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation

A pro-inflammatory role of galectin-3 is indicated by its induction in cells at inflammatory sites, a variety of effects on immune cells (e.g. oxidative burst in neutrophils and chemotaxis in monocytes), and decrease of the inflammatory response, mainly in neutrophils and macrophages, in null mutant mice (in Leffler (editor), 2004b). Moreover, knockout mice of Mac-2BP, a galectin-3 ligand, have increased inflammatory responses (Trahey et al., 1999). Importantly, recent studies have identified galectin-3 as a key rate-limiting factor in macrophage M2 differentiation and myofibroblast activation, which influences the development of fibrosis (Mackinnon et al., 2008; Mackinnon et al., 2012).

Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition to the arsenal available for this.

Treatment of Fibrosis-Related Conditions

The idea of a possible role of galectin-3 in fibrosis comes from cell and ex vivo studies on macrophage differentiation (Mackinnon et al., 2008), as well as from in vivo studies on macrophage differentiation and myofibroblast activation (Mackinnon et al., 2012). Briefly, the hypothesis is as follows: Galectin-3 has been shown to prolong cell surface residence and thus enhance responsiveness of the TGF-β receptor (Partridge et al., 2004), which in turn regulates alternative macrophage differentiation into M2 macrophages and myofibroblast activation. Hence, as galectin-3 is a good candidate for being an endogenous enhancer of TGF-β signaling and alternative macrophage differentiation and myofibroblast activation, galectin-3 inhibitors may be very useful in treating fibrosis and adverse tissue remodeling.

Treatment of Cancer

A large number of immunohistochemical studies show changed expression of certain galectins in cancer (van den Brule et. al. and Bidon et al. in Leffler (editor), 2004b) and for example galectin-3 is now an established histochemical marker of thyroid cancer. The direct evidence for a role of galectin-3 in cancer comes from mouse models, mainly by Raz et al, but also others (in Leffler (editor), 2004b). In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). More recently, inhibition of galectin-3 with small molecules have been demonstrated to indeed greatly enhance tumor cell sensitivity towards radiation and standard pro-apoptotic drugs in cell assays and ex vivo (Lin et al., 2009), as well as in vivo (Glinsky et al., 2009).

Also galectin-1 is frequently over-expressed in low differentiated cancer cells, and galectin-9 or its relatives galectin-4 and galectin-8 may be induced in specific cancer types (Huflejt and Leffler, 2004; Leffler (editor), 2004b). Galectin-1 induces apoptosis in activated T-cells and has a remarkable immunosuppressive effect on autoimmune disease in vivo (Rabinovich et al; and Pace et al. in Leffler (editor), 2004b). Therefore, the over-expression of these galectins in cancers might help the tumor to defend itself against the T-cell response raised by the host.

Null mutant mice for galectins-1 and -3 have been established many years ago (Poirier, 2002). These are healthy and reproduce apparently normally in animal house conditions. However, recent studies have revealed subtle phenotypes in function of neutrophils and macrophages (as described above) and in bone formation for galectin-3 null mutants, and in nerve and muscle cell regeneration/differentiation for the galectin-1 null mutants (Leffler et al., 2004; Poirier, 2002; Watt in Leffler (editor), 2004b). Recently galectin-7 and galectin-9 null mutant mice have been generated and are also grossly healthy in animal house conditions, but have not yet been analyzed in detail. The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Treatment of Angiogenesis

Vascular endothelial growth factors (VEGFs) signaling through VEGF receptor-2 (VEGFR-2) is the primary angiogenic pathway. Studies have been published demonstrating that both galectin-1 (Gal-1) and galectin-3 (Gal-3) are important modulators for VEGF/VEGFR-2 signaling pathway. It has also been published that a galectin inhibitor, TDX, is expected have efficacy against pathological angiogenesis. (Chen 2012)

Known Inhibitors
Natural Ligands

Solid phase binding assays and inhibition assays have identified a number of saccharides and glycoconjugates with the ability to bind galectins (reviewed by Leffler, 2001 and Leffler et al., 2004). All galectins bind lactose with a $K_d$ of 0.5-1 mM. The affinity of D-galactose is 50-100 times lower. N-Acetyl-lactosamine and related disaccharides bind about as well as lactose, but for certain galectins, they can bind either worse or up to 10 times better. The best small saccharide ligands for galectin-3 were those carrying blood group A-determinants attached to lactose or LacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1 (Leffler and Barondes, 1986). A modified plant pectin polysaccharide has been reported to bind galectin-3 (Pienta et al., 1995).

The above-described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of galactose (in e.g. lactose or LacNAc) that bound an extended binding groove. The shape of this groove varies between galectins, suggesting that the same extensions would not be bound equally by the different galectins.

Synthetic Inhibitors

Saccharides coupled to amino acids with anti-cancer activity were first identified as natural compounds in serum, but subsequently, synthetic analogues have been made (Glinsky et al., 1996). Among them, those with lactose or galactose coupled to the amino acid inhibit galectins, but only with about the same potency as the corresponding underivatized sugar. A chemically modified form of citrus pectin (Platt and Raz, 1992) that inhibits galectin-3 shows anti-tumor activity in vivo (Pienta et al., 1995; Nangia-Makker et al., 2002).

Cluster molecules having up to four lactose moieties showed a strong multivalency effect when binding to galectin-3, but not to galectin-1 and galectin-5 (Vrasidas et al., 2003). Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (André et al., 1999) and glycopolymers (Pohl et al., 1999; David et al., 2004), made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules Thiodigalactoside is known to be a synthetic and hydrolytically stable, yet polar inhibitor, approximately as efficient as N-acetyllactosamine (Leffler and Barondes, 1986).

N-Acetyllactosamine derivatives carrying aromatic amides or substituted benzyl ethers at C-3' have been demonstrated to be highly efficient inhibitors of galectin-3, with unprecedented IC$_{50}$ values as low as 4.8 µM, which is a 20-fold improvement in comparison with the natural N-acetyllactosamine disaccharide (Sörme et al., 2002; Sörme et al., 2003b). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, the C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-diamido- or 3,3'-ditriazolyl-derivatization of thiodigalactoside have been developed, (Cumpstey et al., 2005b; Cumpstey et al., 2008; Salameh et al., 2010; WO/2005/113569 and US2007185041; WO/2005/113568, U.S. Pat. No. 7,638,623 B2) which lack O-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise a disadvantage in their multistep synthesis involving double inversion reaction to reach at 3-N-derivatized galactose building blocks. Furthermore, cyclohexane replacement of one galactose ring in thiodigalactoside has been evidenced to mimic the galactose ring and hence to provide galectin-1 and -3 inhibitors with efficiency approaching those of the diamido- and ditriazolyl-thiodigalactoside derivatives (WO/2010/126435). Replacement of a D-galactopyranose unit with a substituted cyclohexane decreases polarity and most likely also metabolic susceptibility, thus improving drug-like properties.

Some earlier described compounds have the following general formulas

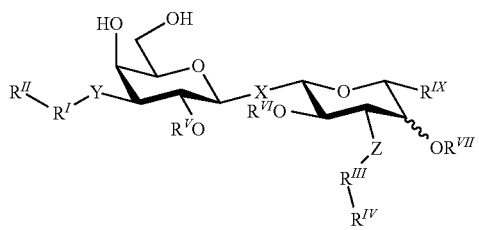

as described in WO/2005/113568, and

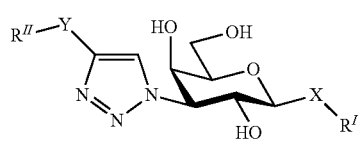

as described in WO/2005/113569, in which R$^1$ can be a D-galactose, and

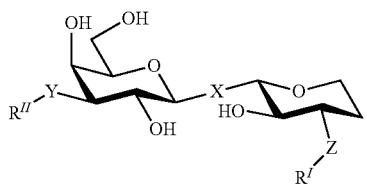

as described in WO/2010/126435.

Thus, due to the less than optimal manufacturing processes towards galactose 3-N-derivatization (Z and Y are preferably nitrogen atoms) involving double inversion reactions at a complex protected D-galactopyranose derivative of the compounds of the prior art, there is still a considerable need within the art of inhibitors against galectins, in particular of galectin-1 and galectin-3.

SUMMARY OF THE INVENTION

Therefore the present invention relates to compounds that are easily manufactured via 3-O-propargyl-galactose derivatives, carry coumarylmethyl moieties at positions O3- and O3'- of thiodigalactoside I and possess galectin-binding activity comparable to compounds known from prior art.

The compounds disclosed herein have the general formula (I)

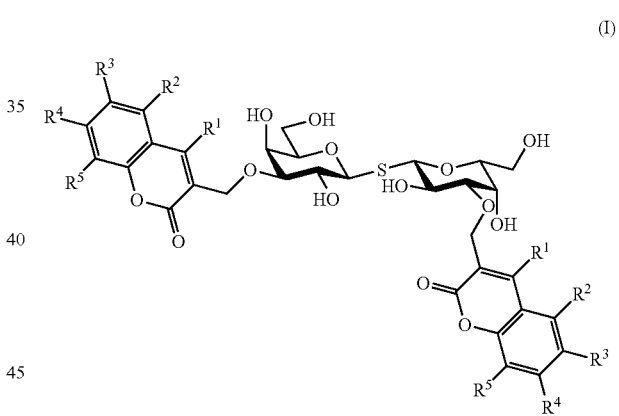

wherein:
R$^1$, R$^2$, R$^3$, R$^4$ and R$^5$ are independently selected from the group consisting of hydrogen, optionally substituted alkyl groups, halogens, optionally substituted alkoxy groups of at least 1 carbon, hydroxyl group, substituted carbonyl groups, optionally substituted acyloxy groups, and optionally substituted amino groups. Two, three, four or five of R$^1$, R$^2$, R$^3$, R$^4$ and R$^5$ in adjacent positions may be linked to form one or more rings, wherein the remaining of R$^1$, R$^2$, R$^3$, R$^4$ and R$^5$ is/are independently selected from the above group.

As evident from structure (I) the configuration of the pyranose rings is β-D-galacto.

The present invention also relates to the above mentioned compounds for use as medicaments.

Furthermore, the present invention relates to pharmaceutical compositions comprising one or more of the above mentioned compounds and at least one pharmaceutically acceptable adjuvant, diluent, excipient and/or carrier.

Furthermore, the present invention relates to the above mentioned compounds for use in the treatment of a disorder relating to the binding of a galectin to a ligand in a mammal.

Furthermore, the present invention relates to the above mentioned compounds for the manufacture of a medicament for the treatment of a disorder relating to the binding of a galectin to a ligand in a mammal.

Furthermore, the present invention relates to methods for treatment of a disorder relating to the binding of a galectin to a ligand in a mammal, wherein a therapeutically effective amount of at least one compound according to any one of the claims 1-4 is administered to a mammal in need of said treatment.

The compounds herein disclosed are mainly galectin-3 inhibitors. However, to some extent at least some of them are also inhibitors of other galectins.

Design of Coumaryl-Substituted Thiodigalactosides as Galectin Inhibitors

Prior art describes different means of attaching affinity-enhancing structural moieties to 3- and 3'-positions of thiodigalactoside. Moieties described are linked via O or N to the thiodigalactoside. However, in order to achieve high affinity for galectins, and galectin-3 in particular, these structural moieties should be aromatic groups linked via N (amide bond or triazolyl ring) to 3- and 3'-positions of thiodigalactoside (Cumpstey et al., 2005b; Cumpstey et al., 2008; Salameh et al., 2010; WO2005113569/US2007185041; WO2005113568, U.S. Pat. No. 7,638,623 B2). Structural moieties linked via O provide inhibitory effects, but with lower affinities (Delaine et al., 2008). The requirement of linking via N to 3- and 3'-positions of thiodigalactoside results in non-optimal prolonged synthetic sequences for introducing the N atom at to 3- and 3'-positions of thiodigalactoside. We have discovered that more easily accessible O-linked structural moieties at 3- and 3'-positions of thiodigalactoside can be obtained via attachment of O-propargyl groups to 3- and 3'-positions of thiodigalactoside. O-Propargyl groups can be converted with known efficient chemical transformations into different heterocyclic aromatic ring systems. Transformation of 3-O-propargyl groups at galactopyranose derivative into coumarylmethyl structures, followed by implementation on a thiodigalactoside formation indeed gave inhibitors with efficiencies in the same range of the prior art 3,3'-diamido- and 3,3'-triazolyl-thiodigalactosides. This is unexpected, because prior art O3- and O3'-linked thiodigalactosides were much less efficient than N-linked derivatives. The unexpected efficiency is apparently due to optimal properties of the substituted (hetero)bicyclic moieties (coumarylmethyl) obtained from a readily accessible O-propargyl-carrying precursor molecule.

DETAILED DESCRIPTION

According to one aspect of the invention, As mentioned above, $R^1$, $R^2$, $R^3$, $R^4$ and $R^5$ are independently selected from the group consisting of hydrogen, optionally substituted alkyl groups, halogens, optionally substituted alkoxy groups of at least 1 carbon, hydroxyl group, substituted carbonyl groups, optionally substituted acyloxy groups, and optionally substituted amino groups.

In the present disclosure, the term "alkyl group" relates to an alkyl group containing 1-7 carbon atoms, which may include one or more unsaturated carbon atoms. In some embodiments the alkyl group contains 1-4 carbon atoms, which may include one or more unsaturated carbon atoms. The carbon atoms in the alkyl group may form a straight or branched chain. The carbon atoms in said alkyl group may also form a cycle containing 3, 4, 5, 6, or 7 carbon atoms. Thus, the term "alkyl group" used herein encompasses methyl, ethyl, n-propyl, isopropyl, n-butyl, sec-butyl, tert-butyl, pentyl, isopentyl, 3-methylbutyl, 2,2-dimethylpropyl, n-hexyl, 2-methylpentyl, 2,2-dimethylbutyl, 2,3-dimethylbutyl, n-heptyl, 2-methylhexyl, 2,2-dimethylpentyl, 2,3-dimethylpentyl, cyclopropyl, cyclobutyl, cyclopentyl, cyclohexyl, cycloheptyl, and 1-methylcyclopropyl.

As mentioned above, if one or more of $R^1$, $R^2$, $R^3$, $R^4$, and $R^5$ is/are an alkyl group, this alkyl group may optionally be substituted. If several of $R^1$, $R^2$, $R^3$, $R^4$ and $R^5$ are alkyl groups, they are optionally substituted independently of each other. This optional substitution means that the alkyl groups may substituted with one, two or more substituents known within the art of organic chemistry. Examples of substituents that may be used for the optionally substituted alkyl groups as herein disclosed are halogen, alkoxy, nitro, sulfo, amino, hydroxy, and carbonyl groups.

In the present disclosure, the term "halogen" refers to a fluoro, a chloro, a bromo or an iodo group.

In the present disclosure, the term "alkoxy group" relates to an alkoxy group containing 1-7 carbon atoms, which may include one or more unsaturated carbon atoms. In some embodiments the alkoxy group contains 1-4 carbon atoms, which may include one or more unsaturated carbon atoms. Thus the term "alkoxy group" encompasses a methoxy group, an ethoxy group, a propoxy group, a isopropoxy group, a n-butoxy group, a sec-butoxy group, tert-butoxy group, pentoxy group, isopentoxy group, 3-methylbutoxy group, 2,2-dimethylpropoxy group, n-hexoxy group, 2-methylpentoxy group, 2,2-dimethylbutoxy group 2,3-dimethylbutoxy group, n-heptoxy group, 2-methylhexoxy group, 2,2-dimethylpentoxy group, 2,3-dimethylpentoxy group, cyclopropoxy group, cyclobutoxy group, cyclopentyloxy group, cyclohexyloxy group, cycloheptyloxy group, and 1-methylcyclopropyloxy group.

As mentioned above, if one or more of $R^1$, $R^2$, $R^3$, $R^4$ and $R^5$ is/are an alkoxy group, this alkyl group may optionally be substituted. If several of $R^1$, $R^2$, $R^3$, $R^4$ and $R^5$ are alkoxy groups, they are optionally substituted independently of each other. This optional substitution means that the alkoxy groups may substituted with one, two or more substituents known within the art of organic chemistry. Examples of substituents that may be used for the optionally substituted alkoxy groups as herein disclosed are halogen, alkoxy, amino, hydroxy, and carbonyl groups.

As mentioned above, one or more of $R^1$, $R^2$, $R^3$, $R^4$ and $R^5$ may be a substituted carbonyl group. Each carbonyl group may be substituted with a substituent known within the art of organic chemistry. Examples of substituents that may be used for the substituted carbonyl groups as herein disclosed are hydrogen, alkyl, aryl, heteroaryl, phenyl, amino, alkoxy, and hydroxyl groups. Said carbonyl group may also incorporate a bi- to polycyclic structures comprising 9-14 carbon atoms, such as 10 carbon atoms. Thus the expression "a substituted carbonyl" in accordance with this disclosure encompasses any of benzoyl, naphthoyl and the like.

In the present disclosure, the term "acyloxy group" relates to a group containing 1-7 carbon atoms, which may include one or more unsaturated carbon atoms. In some embodiments the acyloxy group contains 1-4 carbon atoms, which may include one or more unsaturated carbon atoms. Thus the term "acyloxy group" encompasses an acetoxy group, a propioxy group and the like.

As mentioned above, if one or more of $R^1$, $R^2$, $R^3$, $R^4$ and $R^5$ is/are an acyloxy group, this acyloxy group may optionally be substituted. If several of $R^1$, $R^2$, $R^3$, $R^4$ and $R^5$ are acyloxy groups, they are optionally substituted independently of each other. This optional substitution means that the acyloxy groups may substituted with one, two or more substituents known within the art of organic chemistry. Examples of substituents that may be used for the optionally substituted acyloxy groups as herein disclosed are halogen, alkoxy, amino, hydroxy, and carbonyl groups. Halogen substituents are bromo, fluoro, iodo, and chloro.

As mentioned above, if one or more of $R^1$, $R^2$, $R^3$, $R^4$ and $R^5$ is/are an amino group, this amino group may optionally be substituted. If several of $R^1$, $R^2$, $R^3$, $R^4$ and $R^5$ are amino groups, they are optionally substituted independently of each other. This optional substitution means that the amino groups may be substituted with one, two or more substituents known within the art of organic chemistry. Examples of substituents that may be used for the optionally substituted amino groups as herein disclosed are alkyl, carbonyl, aryl, heteroaryl, and phenyl groups. Said amino group may also incorporate a bi- to polycyclic structures comprising 9-14 carbon atoms, such as 10 carbon atoms. Thus the term substituted amino group will mean any of benzamido, cyclohexylamino, phenylamino and the like.

Furthermore, two, three, four or five of $R^1$, $R^2$, $R^3$, $R^4$ and $R^5$ in adjacent positions may be linked to form one or more rings, wherein the remaining of $R^1$, $R^2$, $R^3$, $R^4$ and $R^5$ is/are independently selected from the above group Such rings may be aliphatic or aromatic and contain heteroatoms. Examples of such rings are benzene, piperidine, cyclopentane, and naphthalene rings. In some embodiments $R^2$ and $R^3$ form a benzene ring.

In some embodiments at least one of $R^1$, $R^2$, $R^3$, $R^4$ and $R^5$ is, independently of the other of $R^1$, $R^2$, $R^3$, $R^4$ and $R^5$, hydrogen. Thus one, two, three, four or all of $R^1$, $R^2$, $R^3$, $R^4$ and $R^5$ may be hydrogen.

In some embodiments at least one of $R^1$, $R^2$, $R^3$, $R^4$ and $R^5$ is independently selected from the group consisting of halogens. Thus, one, two, three, four or all of $R^1$, $R^2$, $R^3$, $R^4$ and $R^5$ may be a halogen.

In some embodiments at least one of $R^1$, $R^2$, $R^3$, $R^4$ and $R^5$ is independently selected from the group consisting of optionally substituted alkoxy groups. Thus, one, two, three, four or all of $R^1$, $R^2$, $R^3$, $R^4$ and $R^5$ may be an optionally substituted alkoxy group.

In some embodiments at least one of $R^1$, $R^2$, $R^3$, $R^4$ and $R^5$ is independently hydroxyl group. Thus, one, two, three, four or all of $R^1$, $R^2$, $R^3$, $R^4$ and $R^5$ may be a hydroxyl group.

In some embodiments at least one of $R^1$, $R^2$, $R^3$, $R^4$ and $R^5$ is independently selected from the group consisting of optionally substituted carbonyl groups. Thus, one, two, three, four or all of $R^1$, $R^2$, $R^3$, $R^4$ and $R^5$ may be an optionally substituted carbonyl group.

In some embodiments at least one of $R^1$, $R^2$, $R^3$, $R^4$ and $R^5$ is independently selected from the group consisting optionally substituted amino groups. Thus, one, two, three, four or all of $R^1$, $R^2$, $R^3$, $R^4$ and $R^5$ may be an optionally substituted amino group.

In some embodiments, the compound of general formula (I) have a $K_d$ against galectin-3 that is less than (i.e. <) 1 µM. In this context, the $K_d$ value is measured in accordance with the test described in Sörme et al, 2003a, 2004.

In some embodiments $R^5$ is hydrogen.

In some embodiments $R^2$ is fluoro while each of $R^1$, $R^3$, $R^4$ and $R^5$ is hydrogen.

In some embodiments $R^3$ is fluoro while each of $R^1$, $R^2$, $R^4$ and $R^5$ is hydrogen.

In some embodiments $R^3$ is a hydroxyl group while each of $R^1$, $R^2$, $R^4$ and $R^5$ is hydrogen.

In some embodiments $R^4$ is a hydroxyl group while each of $R^1$, $R^2$, $R^3$ and $R^5$ is hydrogen.

In some embodiments both $R^2$ and $R^3$ are fluoro, while each of $R^1$, $R^4$ and $R^5$ is hydrogen.

In some embodiments both $R^3$ and $R^4$ are fluoro, while each of $R^1$, $R^2$ and $R^5$ is hydrogen.

In some embodiments $R^2$ is chloro while each of $R^1$, $R^3$, $R^4$, and $R^5$ is hydrogen.

In some embodiments $R^2$ and $R^3$ are linked to form a benzene ring, while each of $R^1$, $R^4$, and $R^5$ is hydrogen.

In some embodiments, all of $R^1$, $R^2$, $R^3$, $R^4$ and $R^5$ in general formula (I) are hydrogen.

In some embodiments, the compound is bis-{3-O-[(2H-1-benzopyran-2-on-3-yl)-methyl]-β-D-galactopyranosyl}sulfane (20).

In some embodiments, the compound is bis-{3-O-[(7-chloro-2H-1-benzopyran-2-on-3-yl)-methyl]-β-D-galactopyranosyl}sulfane (21).

In some embodiments, the compound is bis-{3-O-[(7-methoxy-2H-1-benzopyran-2-on-3-yl)-methyl]-β-D-galactopyranosy}sulfane (22).

In some embodiments, the compound is bis-{3-O-[(7-hydroxy-2H-1-benzopyran-2-on-3-yl)-methyl]-β-D-galactopyranosy}sulfane (23).

In some embodiments, the compound is bis-{3-O-[(6-hydroxy-2H-1-benzopyran-2-on-3-yl)-methyl]-β-D-galactopyranosyl}sulfane (24).

In some embodiments, the compound is bis-{3-O-[(3H-naphtho[2,1-b]pyran-3-on-2-yl)-methyl]-β-D-galactopyranosyl}sulfane (25).

In some embodiments, the compound is bis-{3-O-[(6-tert-butyl-2H-1-benzopyran-2-on-3-yl)-methyl]-β-D-galactopyranosyl}sulfane (26).

In some embodiments, the compound is bis-{3-O-[(6-chloro-2H-1-benzopyran-2-on-3-yl)-methyl]-β-D-galactopyranosyl}sulfane (27).

In some embodiments, the compound is bis-{3-O-[(6-fluoro-2H-1-benzopyran-2-on-3-yl)-methyl]-β-D-galactopyranosyl}sulfane (28).

In some embodiments, the compound is bis-{3-O-[(6,7-difluoro-2H-1-benzopyran-2-on-3-yl)-methyl]-β-D-galactopyranosyl}sulfane (29).

In some embodiments, the compound is bis-{3-O-[(5-chloro-2H-1-benzopyran-2-on-3-yl)-methyl]-β-D-galactopyranosyl}sulfane (30).

In some embodiments, the compound is bis-{3-O-[(5-fluoro-2H-1-benzopyran-2-on-3-yl)-methyl]-β-D-galactopyranosyl}sulfane (31).

In some embodiments, the compound is bis-{3-O-[(5,6-difluoro-2H-1-benzopyran-2-on-3-yl)-methyl]-β-D-galactopyranosyl}sulfane (32).

In some embodiments, the compound is bis-{3-O-[(6-trifluoromethoxy-2H-1-benzopyran-2-on-3-yl)-methyl]-β-D-galactopyranosyl}sulfane (33). In some embodiments, the compound is bis-{3-O-[(7-methyl-2H-1-benzopyran-2-on-3-yl)-methyl]-β-D-galactopyranosy}sulfane (34).

As mentioned above, the pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the pharmaceutical composition.

As mentioned above, the compounds and pharmaceutical compositions herein disclosed may be used for treatment of a disorder relating to the binding of a galectin to a ligand in a mammal.

When the compounds and pharmaceutical compositions herein disclosed are used for the above treatment and/or inhibition, a therapeutically effective amount of at least one compound is administered to a mammal in need of said treatment.

The term "treatment" used herein relates to both treatment in order to cure or alleviate a disease or a condition, and to treatment in order to prevent the development of a disease or a condition. The treatment may either be performed in an acute or in a chronic way.

The term "therapeutically effective amount" relates to an amount that will lead to the desired therapeutic effect.

In some embodiments, the disorder relating to the binding of a galectin to a ligand in a mammal is a disorder dependent on galectin expression.

In this context the term "ligand" relates to a ligand, receptor and/or similar structure to which the galectin binds. Such ligand, receptor and/or similar structure can for example be a glycolipid, a glycoprotein or a proteoglycan.

In some embodiments, the galectin is galectin-3.

In some embodiments, the mammal mentioned above is a human.

In some embodiments the mammal is a human that has been found to have a high level of galectin-3. This may have been detected by using a proprietary or a commercially available test, such as an ELISA or similar antibody based detection system suitable for measurement of galectin-3 in fluids or tissues from said mammal. Galectin-3 levels can be quantitated by performing an immunoassay. A galectin-3 immunoassay involves contacting a sample from a subject to be tested with an appropriate antibody under conditions such that immunospecific binding can occur if galectin-3 is present, and detecting or measuring the amount of any immunospecific binding by the anti-body. Any suitable immunoassay can be used, including, without limitation, competitive and non-competitive assay systems using techniques such as Western blots, radioimmuno-assays, immunohistochemistry, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays and protein A immunoassays. The most common enzyme immunoassay is the "Enzyme-Linked Immunosorbent Assay (ELISA)." ELISA is a technique for detecting and measuring the concentration of an antigen using a labeled (e.g., enzyme-linked) form of the antibody. There are different forms of ELISA, which are well known to those skilled in the art. Standard ELISA techniques are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984), J. Clin. Chem. Clin. Biochem. 22:895-904. A preferred enzyme-linked immunosorbent assay kit (ELISA) for detecting galectin-3 is commercially available (BG Medicine, Waltham, Mass.).

In some embodiments, the disorder relating to the binding of a galectin to a ligand in a mammal is an inflammatory disorder or disease. Examples of such inflammatory disorder or diseases that may be treated according to the invention, or with the compound or pharmaceutical composition according to the invention, are IBD (Inflammatory Bowel Disease), ulcerative colitis, Crohn's disease, SLE (Systemic Lupus Erythematosus, multiple sclerosis.

In some embodiments, the disorder relating to the binding of a galectin to a ligand in a mammal is fibrosis, which may also be denoted fibrotic diseases, conditions or disorders. Example of fibrotic diseases that may be treated according to the invention, or with the compound or pharmaceutical composition according to the invention, are pulmonary fibrosis, liver fibrosis and kidney fibrosis; fibrosis of the heart and heart failure caused by fibrosis, fibrosis of the eye (i.e. ophtamological fibrosis), post-injury fibrosis, post-surgical fibrosis, radiation induced fibrosis, fibrosis associated with inflammatory conditions, fibrosis of the gut, peritoneal fibrosis and fibrosis in any organ compromising the normal function of said organ. One example of pulmonary fibrosis that may be treated according to the invention, or with the compound or pharmaceutical composition according to the invention is idiopathic pulmonary fibrosis.

In some embodiments, the disorder relating to the binding of a galectin to a ligand in a mammal is septic shock.

In some embodiments, the disorder relating to the binding of a galectin to a ligand in a mammal is cancer, including cancer metastases.

In some embodiments, the disorder relating to the binding of a galectin to a ligand in a mammal is an autoimmune disease. Examples of autoimmune diseases that may be treated according to the invention, or with the compound or pharmaceutical composition according to the invention, are rheumatoid arthritis and multiple sclerosis.

In some embodiments, the disorder relating to the binding of a galectin to a ligand in a mammal is a metabolic disorder. One examples of metabolic disorder that may be treated according to the invention, or with the compound or pharmaceutical composition according to the invention, is diabetes.

In some embodiments, the disorder relating to the binding of a galectin to a ligand in a mammal is heart disease or heart failure.

In some embodiments, the disorder relating to the binding of a galectin to a ligand in a mammal is pathological angiogenesis. Examples of pathological angiogenesis that may be treated according to the invention, or with the compound or pharmaceutical composition according to the invention, are ocular angiogenesis, disease or conditions associated with ocular angiogenesis and cancer.

In some embodiments, the disorder relating to the binding of a galectin to a ligand in a mammal is an eye disease. Examples of eye disease that may be treated according to the invention, or with the compound or pharmaceutical composition according to the invention, are ocular angiogenesis and disease or conditions associated with ocular angiogenesis, as mentioned above, and also related macular degeneration and corneal neovascularization.

In some embodiments only one compound as herein disclosed is used for the purposes discussed above.

In some embodiments two or more of the compound as herein disclosed are used in combination for the purposes discussed above.

The pharmaceutical composition according to the present invention comprising a compound of the invention may be adapted for oral, intravenous, topical, intraperitoneal, nasal, buccal, sublingual, or subcutaneous administration, or for administration via the respiratory tract in the form of, for example, an aerosol or an air-suspended fine powder, or, for administration via the eye, intra-ocularly, intravitreally or corneally. Therefore, the pharmaceutical composition of the present invention may be in the form of, for example, tablets, capsules, powders, solutions for injection, solutions for spraying, ointments, transdermal patches or suppositories. Alternatively, in particular for treatment of different diseases or disorders affecting the eye, the pharmaceutical composition according to the invention may be in the form of eye drops, eye gels, eye sprays or eye patches.

The pharmaceutical composition of the present invention may optionally comprise two or more compounds of the present invention. The composition may also be used together with other medicaments within the art for the treatment of related disorders.

The typical dosages of the compounds of the present invention vary within a wide range and depend on many factors, such as the route of administration, the requirement of the individual in need of treatment, the individual's body weight, age and general condition.

The adjuvants, diluents, excipients and/or carriers that may be used in the composition of the invention must be pharmaceutically acceptable in the sense of being compatible with the compounds and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

EXAMPLES

Synthesis of Coumaryl-Substituted Thiodigalactosides

The coumaryl-substituted thiodigalactosides were synthesized from known phenyl 3-O-propargyl-1-thio-β-D-galactopyranoside 1 (Giguere et al., 2006) as shown in scheme 1.

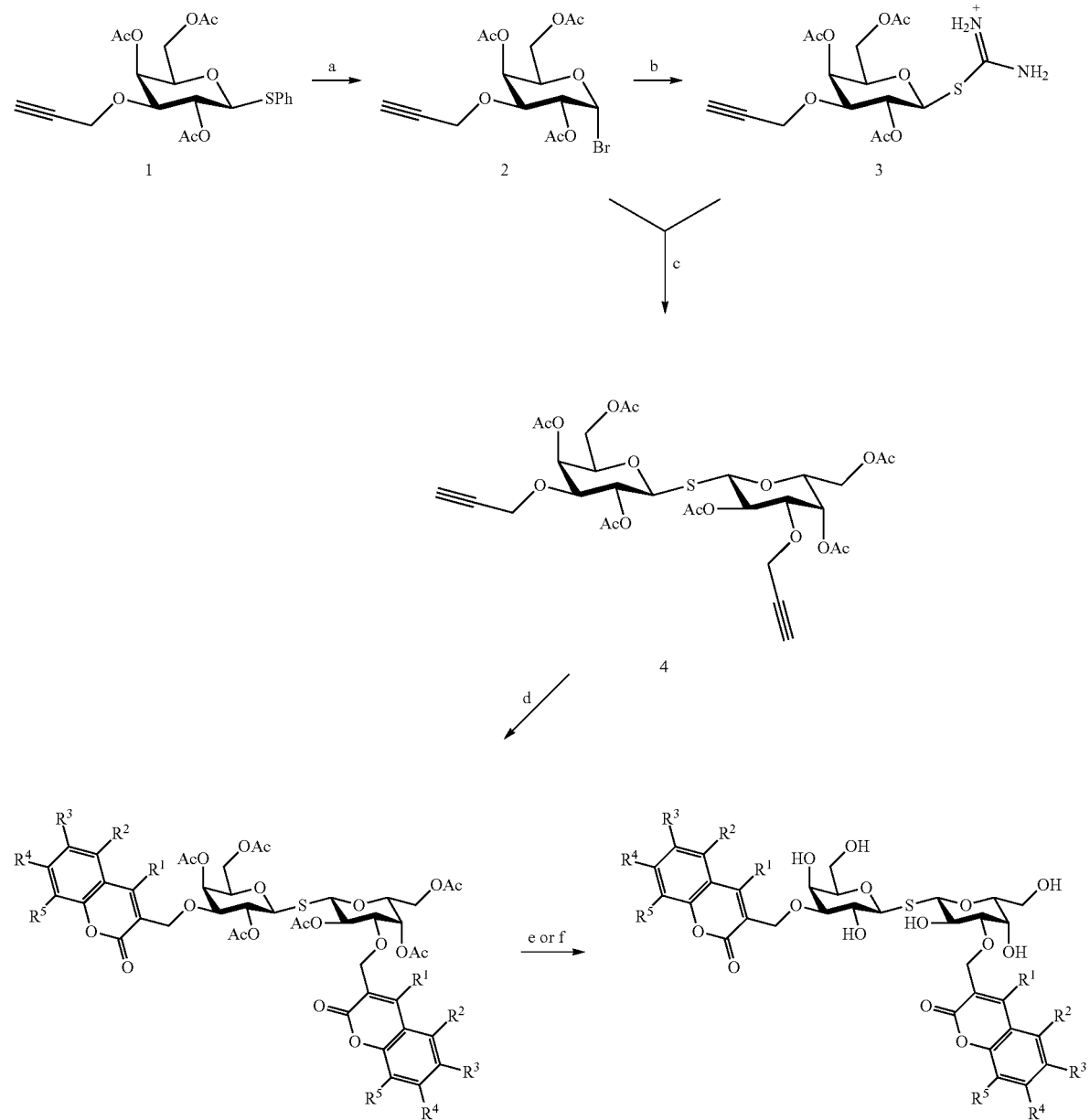

5 $R^1$-$R^5$ = H
6 $R^4$ = Cl, $R^1$ = $R^2$ = $R^3$ = $R^5$ = H
7 $R^4$ = OCH$_3$, $R^1$ = $R^2$ = $R^3$ = $R^5$ = H
8 $R^4$ = OH, $R^1$ = $R^2$ = $R^3$ = $R^5$ = H
9 $R^3$ = OH, $R^1$ = $R^2$ = $R^4$ = $R^5$ = H
10 $R^2$, $R^3$ = Ph, $R^1$ = $R^4$ = $R^5$ = H
11 $R^3$ = tBu, $R^1$ = $R^2$ = $R^4$ = $R^5$ = H
12 $R^3$ = Cl, $R^1$ = $R^2$ = $R^4$ = $R^5$ = H
13 $R^3$ = F, $R^1$ = $R^2$ = $R^4$ = $R^5$ = H
14 $R^3$ = $R^4$ = F, $R^1$ = $R^2$ = $R^5$ = H
15 $R^2$ = Cl, $R^1$ = $R^3$ = $R^4$ = $R^5$ = H
16 $R^2$ = F, $R^1$ = $R^3$ = $R^4$ = $R^5$ = H
17 $R^2$ = $R^3$ = F, $R^1$ = $R^4$ = $R^5$ = H
18 $R^3$ = OCF$_3$, $R^1$ = $R^2$ = $R^4$ = $R^5$ = H
19 $R^4$ = CH$_3$, $R^1$ = $R^2$ = $R^3$ = $R^5$ = H

20 $R^1$-$R^5$ = H
21 $R^4$ = Cl, $R^1$ = $R^2$ = $R^3$ = $R^5$ = H
22 $R^4$ = OCH$_3$, $R^1$ = $R^2$ = $R^3$ = $R^5$ = H
23 $R^4$ = OH, $R^1$ = $R^2$ = $R^3$ = $R^5$ = H
24 $R^3$ = OH, $R^1$ = $R^2$ = $R^4$ = $R^5$ = H
25 $R^2$, $R^3$ = Ph, $R^1$ = $R^4$ = $R^5$ = H
26 $R^3$ = tBu, $R^1$ = $R^2$ = $R^4$ = $R^5$ = H
27 $R^3$ = Cl, $R^1$ = $R^2$ = $R^4$ = $R^5$ = H
28 $R^3$ = F, $R^1$ = $R^2$ = $R^4$ = $R^5$ = H
29 $R^3$ = $R^4$ = F, $R^1$ = $R^2$ = $R^5$ = H
30 $R^2$ = Cl, $R^1$ = $R^3$ = $R^4$ = $R^5$ = H
31 $R^2$ = F, $R^1$ = $R^3$ = $R^4$ = $R^5$ = H
32 $R^2$ = $R^3$ = F, $R^1$ = $R^4$ = $R^5$ = H
33 $R^3$ = OCF$_3$, $R^1$ = $R^2$ = $R^4$ = $R^5$ = H
34 $R^4$ = CH$_3$, $R^1$ = $R^2$ = $R^3$ = $R^5$ = H a) Br$_2$, CH$_2$Cl$_2$; b) Thiourea, MeCN; c) Et$_3$N, MeCN; d) TsN$_3$, CuI, Salicaldehyde or acetophenone derivative, THF; e) NaOMe, MeOH; f) AcCl, MeOH Evaluation of $K_d$ Values Against Galectin-3

Compounds 20-34 were evaluated for their efficiency in inhibiting galectin-1 and galectin-3 in a known fluorescence polarization-based assay (Sorme et al., 2003a, 2004) (see also Table 1 below). The known galectin inhibitors methyl β-D-galactoside and thiodigalactoside were included as reference compounds. Indeed, all compounds were potent inhibitors of galectin-1 and galectin-3 with dissociation constant in the low μM or nM range. This evidences that a synthetically simple and properly structured coumaryl substituents on O3 and O3' of thiodigalactoside show inhibitory efficiencies in the range of comparable 3-N-substituted and synthetically earlier known compounds (3,3'-amido-thiodigalctosides; such as the closely related 36) and significantly better that the comparable earlier known best 3-O-substituted compounds (3,3'-diester thiodigalactoside 35) when evaluated in the same assay.

The unexpectedly high inhibitor potency of 20, 23-24, and 28-32, in the range of the best prior art, together with the significantly simplified synthetic route via easily accessible 3-O-propargyl-galactose derivatives, render the 3-O-coumaryl-substituted thiodigalactosides suitable as active components in pharmaceutical compositions targeting conditions where galectin-3 plays a pathogenic role.

TABLE 1
Affinity of compounds for galectin-1,3,7,8 (N-terminal domain), and 9 (N-terminal domain)
| Cpd # | Structure | Calculated Kd (μM) Galectin | | | | | | | | |
|---|---|---|---|---|---|---|---|---|---|---|
| | | 1 | 3 | 4 (N-terminal domain) | 4 (C-terminal domain) | 7 | 8 (N-terminal domain) | 9 (N-terminal domain) | 9 (C-terminal domain) |
| 1 | 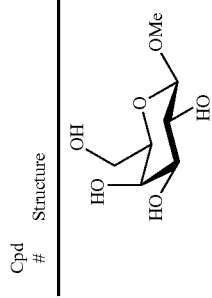<br>Reference compound | >10000 | 4400 | 6600 | >10000 | 4800 | 5200 | 3400 | 5000 |
| 2 | 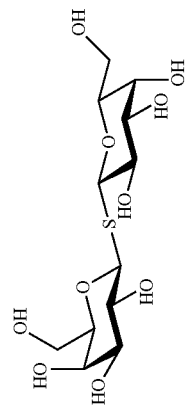<br>Reference compound | 24 | 49 | 440 | 940 | 160 | 61 | 38 | 44 |

TABLE 1-continued

Affinity of compounds for galectin-1,3,7,8 (N-terminal domain), and 9 (N-terminal domain)

| Cpd # | Structure | Calculated Kd (µM) Galectin | | | | | | | |
|---|---|---|---|---|---|---|---|---|---|
| | | 1 | 3 | 4 (N-terminal domain) | 4 (C-terminal domain) | 7 | 8 (N-terminal domain) | 9 (N-terminal domain) | 9 (C-terminal domain) |
| 20 | (structure) | 15.4 | 0.25 | 49 | 156 | 3.9 | 11 | 1.7 | 2.4 |
| 21 | (structure) | 21 | 4.7 | na* | na | 61 | 74 | 140 | na |

TABLE 1-continued

Affinity of compounds for galectin-1,3,7,8 (N-terminal domain), and 9 (N-terminal domain)

| Cpd # | Structure | Calculated Kd (µM) Galectin | | | | | | | |
|---|---|---|---|---|---|---|---|---|---|
| | | 1 | 3 | 4 (N-terminal domain) | 4 (C-terminal domain) | 7 | 8 (N-terminal domain) | 9 (N-terminal domain) | 9 (C-terminal domain) |
| 22 | | 9.9 | 0.89 | 130 | >500 | 37 | 85 | 13 | ≈4.0 |
| 23 | | 3.9 | 0.076 | 32 | >300 | na | 40 | 1.5 | na |

TABLE 1-continued

Affinity of compounds for galectin-1,3,7,8 (N-terminal domain), and 9 (N-terminal domain)

| Cpd # | Structure | Calculated Kd (µM) Galectin | | | | | | | |
|---|---|---|---|---|---|---|---|---|---|
| | | 1 | 3 | 4 (N-terminal domain) | 4 (C-terminal domain) | 7 | 8 (N-terminal domain) | 9 (N-terminal domain) | 9 (C-terminal domain) |
| 24 | 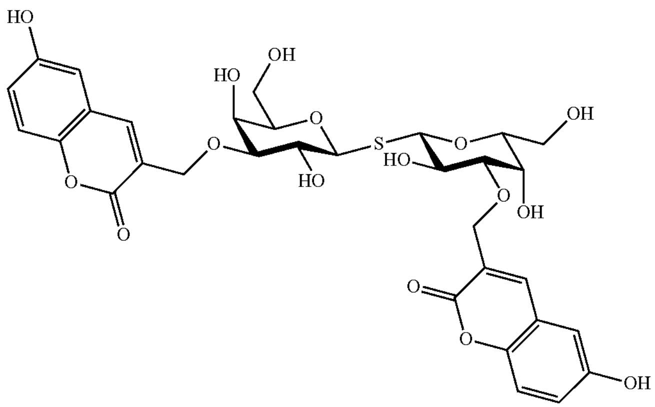 | 20 | 0.15 | 180 | >300 | na | 140 | 8.9 | na |
| 25 | 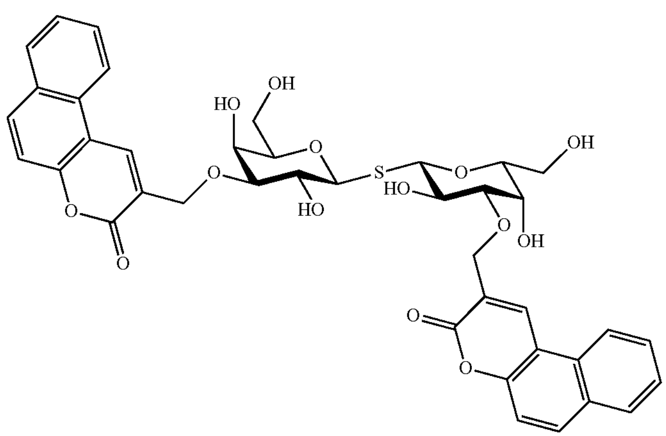 | 22 | 0.51 | 110 | >300 | na | >300 | 4.7 | na |

TABLE 1-continued

Affinity of compounds for galectin-1,3,7,8 (N-terminal domain), and 9 (N-terminal domain)

| Cpd # | Structure | Calculated Kd (μM) Galectin | | | | | | | |
|---|---|---|---|---|---|---|---|---|---|
| | | 1 | 3 | 4 (N-terminal domain) | 4 (C-terminal domain) | 7 | 8 (N-terminal domain) | 9 (N-terminal domain) | 9 (C-terminal domain) |
| 26 | [structure with tBu-coumarin groups] | 25 | 8.1 | >1000 | >>1000 | na | 62 | 39 | 17 |
| 27 | [structure with Cl-coumarin groups] | 7.9 | 6.0 | 430 | 100 | na | 34 | >200 | 86 |

TABLE 1-continued

Affinity of compounds for galectin-1,3,7,8 (N-terminal domain), and 9 (N-terminal domain)

| Cpd # | Structure | Calculated Kd (μM) Galectin | | | | | | | |
|---|---|---|---|---|---|---|---|---|---|
| | | 1 | 3 | 4 (N-terminal domain) | 4 (C-terminal domain) | 7 | 8 (N-terminal domain) | 9 (N-terminal domain) | 9 (C-terminal domain) |
| 28 | 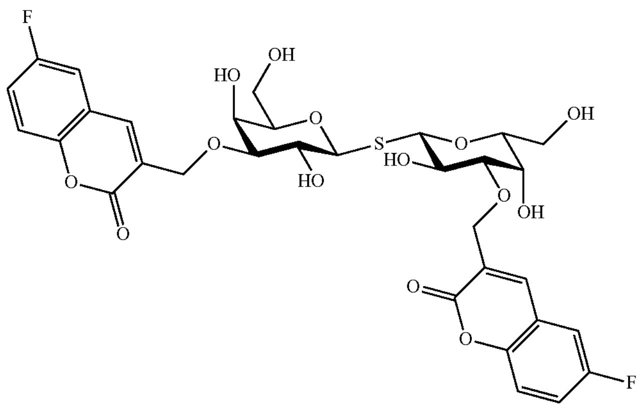 | 3.4 | 0.097 | 180 | >>1000 | na | 47 | 3.5 | 7.9 |
| 29 | 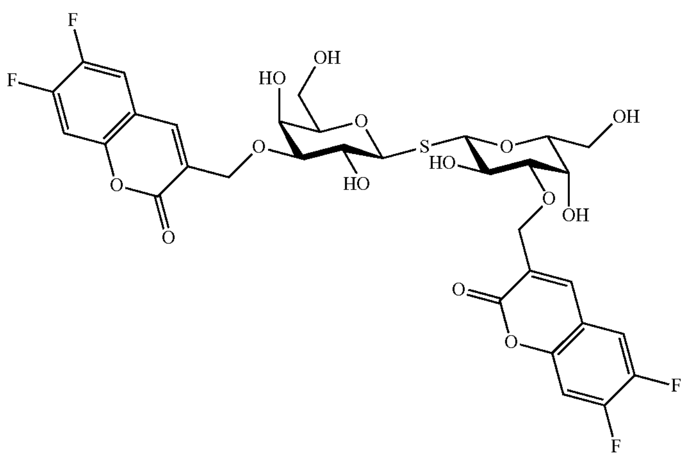 | 1.6 | 0.11 | 44 | 220 | na | 19 | 3.0 | 2.3 |

TABLE 1-continued

Affinity of compounds for galectin-1,3,7,8 (N-terminal domain), and 9 (N-terminal domain)

| Cpd # | Structure | Calculated Kd (μM) Galectin | | | | | | | |
|---|---|---|---|---|---|---|---|---|---|
| | | 1 | 3 | 4 (N-terminal domain) | 4 (C-terminal domain) | 7 | 8 (N-terminal domain) | 9 (N-terminal domain) | 9 (C-terminal domain) |
| 30 | ![structure] | 25 | 0.17 | 55 | >>1000 | na | 28 | 54 | 16 |
| 31 | ![structure] | 8.7 | 0.061 | 46 | 540 | na | 28 | 7.0 | 5.5 |

TABLE 1-continued

Affinity of compounds for galectin-1,3,7,8 (N-terminal domain), and 9 (N-terminal domain)

| Cpd # | Structure | Calculated Kd (µM) Galectin | | | | | | | |
|---|---|---|---|---|---|---|---|---|---|
| | | 1 | 3 | 4 (N-terminal domain) | 4 (C-terminal domain) | 7 | 8 (N-terminal domain) | 9 (N-terminal domain) | 9 (C-terminal domain) |
| 32 | 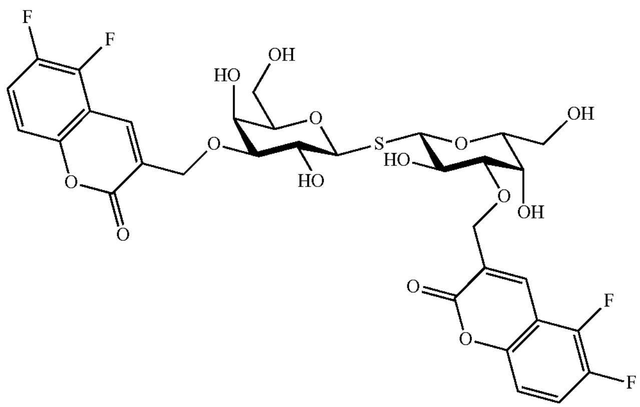 | 3.9 | 0.032 | 22 | >500 | na | 41 | 1.1 | 1.5 |
| 33 | 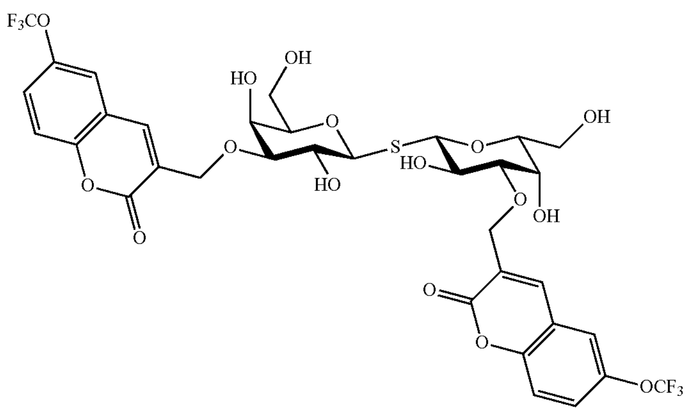 | 84 | 0.95 | >500 | >500 | na | 110 | 29 | 21 |

TABLE 1-continued

Affinity of compounds for galectin-1,3,7,8 (N-terminal domain), and 9 (N-terminal domain)

| Cpd # | Structure | Calculated Kd (µM) Galectin | | | | | | | | |
|---|---|---|---|---|---|---|---|---|---|---|
| | | 1 | 3 | 4 (N-terminal domain) | 4 (C-terminal domain) | 7 | 8 (N-terminal domain) | 9 (N-terminal domain) | 9 (C-terminal domain) | |
| 34 | 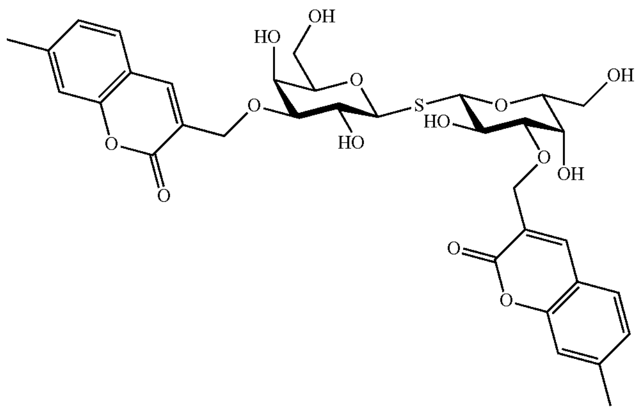 | 200 | 9.4 | >500 | >500 | na | >700 | >200 | >500 | |
| 35 | 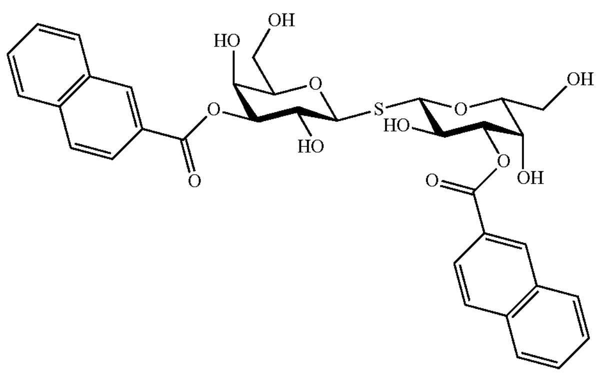 | 14.7 | 10.7 | na | na | 48 | 100 | 2.8 | na | Comparative compound (Delaine et al., 2008; WO2005113569/US2007185041) |

TABLE 1-continued

Affinity of compounds for galectin-1,3,7,8 (N-terminal domain), and 9 (N-terminal domain)

| Cpd # | Structure | Calculated Kd (μM) Galectin | | | | | | | |
|---|---|---|---|---|---|---|---|---|---|
| | | 1 | 3 | 4 (N-terminal domain) | 4 (C-terminal domain) | 7 | 8 (N-terminal domain) | 9 (N-terminal domain) | 9 (C-terminal domain) |
| 36 | Comparative compound (Cumpstey et al., 2005b; Cumpstey et. al., 2008; WO2005113569/US2007185041) | 9.6 | 0.16 | na | na | 1.7 | >100 | 0.73 | na |

*na = not available;
> = more than;
>> = much more than;
≈ = approximately

Methodology/Experimental

General Synthetic Procedures

The compounds as herein disclosed may be prepared by the below mentioned general methods and procedures. The galectin-1 assays galectin-3 assays, galectin-7 assays, galectin-8 assays and galectin-9 assays used herein may be performed by the below mentioned general methods and procedures. It should be appreciated that where typical or preferred process conditions (e.g. reaction temperatures, times, molar ratios of reactants, solvents, pressures, pH etc) are given, other process conditions may also be used unless otherwise stated. Optimum reaction conditions may vary with the particular reactants, solvents used and pH etc., but such conditions can be determined by one skilled in the art by routine optimization procedures.

Identification of the substances was made by HRMS (Micromass Q-tof micro) and NMR (Bruker Ultrashield 400 plus, 400 MHz). Chemical shifts are reported downfield from $Me_4Si$ using residual $CHD_2Cl$ (7.26 ppm) or $CHD_2OD$ (3.35 ppm) as reference. Chemical shifts and coupling constants were obtained from $^1$H-NMR and proton resonances were assigned from COSY experiments. Purification was made by RF-HPLC (Beckman, system gold) or flash chromatography, using silica gel (Davisil 35-70 μm, 60 Å). Reactions were followed by TLC (Aluminum sheet, silica gel 60 F254) visualized with UV light, $H_2SO_4$ (aq) or an iso-vanillin/$H_2SO_4$/EtOH development solution. THF and $Et_2O$ were dried over sodium/benzophenone and distilled. $CH_2Cl_2$ was dried by molecular sieves (4 Å, 1.6 mm). Other solvents and reagents were commercially available and used without further purifications. Fluorescence polarization experiments were performed on a PolarStar instrument (BMG, Offenburg; Germany). Evaluation of 20-34 as inhibitors of galectins was performed by use of fluorescence polarization as described in the literature (Sorme et al., 2003a, 2004). Galectin concentrations and fluorescent probe choice and concentrations were as described in Cumpstey et al. 2005a, except for galectin-3 for which the probe tdga-probe described in Salomonsson et al. 2010 was used at 20 nM together with galectin-3 at 200 nM concentrations. Each inhibitor was tested in duplicate at several concentrations between 4 and 0.25 μM. All fluorescence polarization experiments were conducted at 20° C., except galectin-7 for which experiments were conducted at 0° C.

Synthesis of di-(3-O-propargyl-β-D-galactopyranosyl)-sulfane (Compound 4)

To a solution of compound 1 (2.0 g, 4.58 mmol, Giguere et al. 2006) in dry dichloromethane (20 mL) was added molecular bromine (0.26 mL, 5.04 mmol) and the solution was stirred at 0° C. for 15 min when the TLC showed complete conversion of the starting material to a slightly faster moving component. The excess bromine was neutralized with cyclopentene and the solvents were evaporated in vacuo. The residue was purified by flash chromatography using n-hexane-EtOAc (2:1) to afford pure compound 2 (1.52 g, 82%) as colourless thick syrup. Having concerned with susceptible stability of compound 2, it was considered in further reaction without its analytical characterization. To the half amount (0.76 g, 1.87 mmol) of compound 2 in dry acetonitrile (15 ml) was added thiourea (0.14 g, 1.86 mmol) under continuous flow of nitrogen and the mixture was allowed to reflux at 80° C. for 4 h when the TLC using mobile phase n-hexane-EtOAc (2:1) confirmed full consumption of 2 to slower moving spot. The reaction mixture was allowed to cool to room temp and subsequently a solution of the second half of compound 2 (0.76 g, 1.87 mmol) in dry acetonitrile was added to the reaction under nitrogen atmosphere followed by catalytic amount of $Et_3N$ and reaction was allowed to stir for overnight. The completion of the reaction was confirmed by TLC (mobile phase n-hexane-EtOAc (1:1). The solvents were evaporated in vacuo. The residue was purified by flash chromatography using n-hexane-EtOAc (1:1) to afford pure compound 4 (0.92 g, 72%) as a white solid.

General Experimental Procedure for the Synthesis of Coumarines 20-34

A solution of 4 (1 mmol), tosyl azide (Waser et al. 2006) (2 mmol), CuI (0.1 mmol) and salicylaldehyde (2.2 mmol) in dry THF (5 mL) in a 25 mL round bottomed flask is stirred under nitrogen for 1 hour. $Et_3N$ (2 mmol) is then added slowly via syringe. The resulting solution is allowed to stir at room temperature for 12-24 hours until TLC analysis shows complete conversion of 4 (n-hexane-EtOAc). Solvents are evaporated in vacuo and the residue is dissolved in $CH_2Cl_2$ (10 mL) and washed successively with aqueous $NH_4Cl$ (2×10 mL) and brine (10 mL). The organic layer is separated, dried ($Na_2SO_4$) and evaporated in vacuo. The residue is purified by flash chromatography using n-hexane-EtOAc as eluent to give compounds 5-19. For compounds 5-7 and 10-19, the residue is dissolved in methanol (50 mL) and methanolic sodium methoxide (0.1 mL, 1 M) is added. (In some cases dichloromethane (10 mL) is added to obtain a clear reaction solution.) Water (0.4 mL) is added after 12-24 hours and after another 12-24 hours the reaction is concentrated. Column chromatography ($SiO_2$, dichloromethane/methanol, 11:1) afforded >95% pure 20-22 and 25-34. For compounds 8 and 9 the residue is dissolved in methanol/dichloromethane (1:1, 50 mL) and AcCl (5.5 mL) is added slowly. When TLC analysis shows the reaction to be complete (after 2-6 days), the reaction is concentrated. Column chromatography ($SiO_2$, dichloromethane/methanol, 5:1) afforded >95% pure 23-24.

Selected specific experimental procedure for the synthesis of methoxy-derivative bis-{3-O-[(7-methoxy-2H-1-benzopyran-2-on-3-yl)-methyl]-β-D-galactopyranosyl}sulfane (22)

Compound 4 (100 mg, 0.14 mmol) was dissolved in dry THF (5 mL). CuI (5.54 mg, 0.029 mmol), 4-methoxy-salicylaldehyde (52.9 mg, 0.35 mmol), $TsN_3$ (68.6 mg, 0.35 mmol) were added to the above solution and the reaction was stirred under nitrogen at room temperature. After 1 h, $Et_3N$ (80 μL, 0.58 mmol) was injected slowly and the resulting solution was allowed to stir at room temperature for 12 h when TLC showed complete conversion of 4 (n-hexane-EtOAc, 1:3)). Solvents were evaporated in vacuo and the residue was dissolved in $CH_2Cl_2$ (10 mL) and washed successively with aqueous $NH_4Cl$ (2×10 mL) and brine (10 mL). The organic layer was separated, dried ($Na_2SO_4$) and evaporated in vacuo. The residue was dissolved in MeOH and NaOMe was added to it with few drops of $CH_2Cl_2$ to make the clear solution. The reaction mixture was stirred for 12 h and then added 0.4 mL of water and again left the reaction mixture at room temperature for 12 h. After the completion of the reaction, it was neutralized with DOWEX H$^+$ resin. Filtered the reaction mixture and evaporated the solvent in vacuo. The residue was purified by flash chromatography ($SiO_2$, dichloromethane/methanol, 10:1) to afford pure compound 22 (85 mg, 83%).

Selected Specific Experimental Procedure for the Synthesis of methoxy-derivative bis-{3-O-[(5,6-difluoro-2H-1-benzopyran-2-on-3-yl)-methyl]-β-D-galactopyranosyl}sulfane (32)

Compound 4 (300 mg, 0.437 mmol) and CuI (16.6 mg, 0.087 mmol) were stirred in dry THF (3 mL) under argon. 5,6-Difluoro-salicylaldehyde (166 mg, 1.05 mmol) and $Et_3N$ (146 μL, 1.05 mmol) were added, followed by dropwise addition of $TsN_3$ (207 mg, 1.05 mmol). After 1.5 h at 20° C., silica gel (1.5 g) was added and solvents were evaporated in vacuo providing a free flowing solid. Purification was performed by flash column chromatography, loading the material onto a silica gel column (25 g) and eluting with 0→25% acetone in toluene. The product was obtained as an off-white powder (500 mg). The residue (500 mg, 0.383 mmol) was dissolved in $CH_2Cl_2$ (20 mL) and methanol (20 mL). A 25 wt % solution of sodium methoxide in methanol was added dropwise to pH 11. The mixture was stirred for 18 h at 20° C. Water (80 μL) was charged and the mixture was stirred for a further 24 h. The reaction was neutralised by the addition of solid $CO_2$ pellets, then silica gel (1.2 g) was added. The mixture was concentrated in vacuo to provide a free flowing solid. Purification was performed by flash column chromatography, loading the material onto a silica gel column (25 g) and eluting with 0→25% methanol in $CH_2Cl_2$. The product 32 was isolated as a white solid (105 mg, 29%).

Data for Obtained Compounds

Bis-{3-O-[(2H-1-benzopyran-2-on-3-yl)-methyl]-β-D-galactopyranosy}sulfane (20)

$^1$H NMR (DMSO-$d_6$, 400 MHz) δ: 8.21 (s, 2H, ArH), 7.68 (d, 2H, J 7.6 Hz, ArH), 7.59 (m, 2H, ArH), 7.39 (m, 4H, ArH), 4.61-4.54 (m, 6H, $CH_2Ar$, H-1), 4.02 (bs, 2H, H-4), 3.60 (t, 2H, J 9.6 Hz, H-2), 3.52 (m, 4H, H-6$^a$, H-6$^b$), 3.39 (m, 4H, H-3, H-5). $^{13}$C NMR (DMSO-$d_6$, 100 MHz) δ: 159.7, 152.5, 138.6, 131.3, 128.1, 126.2, 124.7, 119.1, 116.1 (ArC) 83.2 (C-1), 82.6, 78.9, 69.2, 65.2, 65.0, 60.3. HRMS calculated for $C_{32}H_{34}NaO_{14}S$ (M+Na)$^+$: 695.1567; found 697.1582.

Bis-{3-O-[(7-chloro-2H-1-benzopyran-2-on-3-yl)-methyl]-β-D-galactopyranosyl}sulfane (21)

$^1$H NMR (DMSO-$d_6$, 400 MHz) δ: 8.20 (s, 2H, ArH), 7.77 (bs, 2H, ArH), 7.64 (m, 2H, ArH), 7.48 (d, 2H, J 9.2 Hz, ArH), 4.46-4.53 (m, 6H, $CH_2Ar$, H-1), 4.03 (bs, 2H, H-4), 3.64-3.35 (m, 8H, H-2, H-6a, H-6$^b$, H-3, H-5). $^{13}$C NMR (DMSO-$d_6$, 100 MHz) δ: 159.7, 151.4, 137.7, 131.1, 128.7, 127.8, 127.4, 120.7, 118.4 (ArC) 83.4 (C-1), 82.6, 79.1, 69.4, 65.6, 65.3, 60.6. HRMS calculated for $C_{32}H_{32}Cl_2O_{14}SNa$ (M+Na)$^+$: 765.0788. found 765.0791.

Bis-{3-O-[(7-methoxy-2H-1-benzopyran-2-on-3-yl)-methyl]-β-D-galactopyranosy}sulfane (22)

$^1$H NMR (DMSO-$d_6$, 400 MHz) δ: 8.15 (s, 2H, ArH), 7.60 (d, 2H, J 8.8 Hz, ArH), 7.03 (d, 2H, J 8.6 Hz, ArH), 6.98 (dd, 4H, J 2.5, 8.6 Hz, ArH), 5.20 (brs, 2H, HO-2), 4.61 (d, 2H, J 10 Hz, H-1), 4.51 (bABq, 4H, J 14.8 Hz, $CH_2Ar$), 4.03 (bs, 2H, H-4), 3.84 (s, 6H, $OCH_3$), 3.63-3.48 (m, 6H, H-2, H-6a, H-6$^b$), 3.36 (m, 4H, H-3, H-5). $^{13}$C NMR (DMSO-$d_6$, 100 MHz) δ: 162.2, 160.4, 154.6, 139.5, 129.3, 122.4, 112.8, 100.7 (ArC) 83.2 (C-1), 82.8, 79.0, 69.3, 65.4, 65.1, 60.4, 56.1 ($OCH_3$). HRMS calculated for $C_{34}H_{38}O_{16}SNa$ (M+Na)$^+$: 757.1778. found 757.1781.

Bis-{3-O-[(7-hydroxy-2H-1-benzopyran-2-on-3-yl)-methyl]-β-D-galactopyranosy}sulfane (23)

$^1$H NMR (DMSO-$d_6$, 400 MHz) δ: 10.49 (s, 2H, HO—Ar), 8.11 (s, 2H, ArH), 7.50 (d, 2H, J 8.0 Hz, ArH), 6.82 (dd, 2H, J 2.4 Hz, 8.4 Hz, ArH), 6.74 (d, 2H, J 2.0 Hz, ArH), 5.20 (d, 2H, J 6.0 Hz, HO-2), 4.62 (m, 6H, H-1, HO-4, HO-6), 4.54 (ABq, 4H, J 14.4 Hz, $CH_2Ar$), 4.02 (br s, 2H, H-4), 3.60 (m, 6H, H-2, H-6), 3.39 (m, 4H, H-3, H-5). LRMS (ESI) m/z: 729.1 [M+Na]$^+$

Bis-{3-O-[(6-hydroxy-2H-1-benzopyran-2-on-3-yl)-methyl]-β-D-galactopyranosy}sulfane (24)

$^1$H NMR (DMSO-$d_6$, 400 MHz) δ: 9.73 (s, 2H, HO—Ar), 8.14 (s, 2H, ArH), 7.27 (d, 2H, J 8.8 Hz, ArH), 7.02 (m, 4H, J 2.8 Hz, 8.8 Hz, ArH), 5.26 (d, 2H, J 5.6 Hz, HO-2), 4.64 (m, 6H, H-1, HO-4, HO-6), 4.58 (ABq, 4H, J 15.2 Hz, $CH_2Ar$), 4.02 (br s, 2H, H-4), 3.65 (m, 2H, H-2), 3.52 (m, 4H, H-6), 3.39 (m, 4H, H-3, H-5). LRMS (ESI) m/z: 729.2 [M+Na]$^+$.

Bis-{3-O-[(3H-naphtho[2,1-b]pyran-3-on-2-yl)-methyl]-β-D-galactopyranosyl}sulfane (25)

$^1$H NMR (DMSO-$d_6$, 400 MHz) δ: 9.09 (s, 2H, ArH), 8.61 (d, 2H, J 8 Hz, ArH), 8.18 (d, 2H, J 8.8 Hz, ArH), 8.08 (d, 2H, J 8.0 Hz, ArH), 7.79 (m, 2H, J 8.0 Hz, ArH), 7.65 (m, 2H, J 8.0 Hz, ArH), 7.62 (d, 2H, J 8.8 Hz, ArH), 5.60 (d, 2H, J 5.6 Hz, HO-2), 4.79 (d, 2H, J 4.8 Hz, HO-4), 4.67 (m, 8H, H-1, $CH_2Ar$, HO-6), 4.09 (br s, 2H, H-4), 3.76 (m, 2H, H-2), 3.58 (m, 4H, H-6), 3.47 (m, 4H, H-3, H-5). LRMS (ESI) m/z: 796.9 [M+Na]$^+$.

Bis-{3-O-[(6-tert-butyl-2H-1-benzopyran-2-on-3-yl)-methyl]-β-D-galactopyranosy}sulfane (26)

$^1$H NMR ($CD_3OD$, 400 MHz) δ: 8.08 (s, 2H, ArH), 7.55 (dd, 2H, J 2.4, 7.2, Hz, ArH), 7.53 (s, 2H, ArH), 7.17 (m, 2H, ArH), 4.64 (d, 2H, J 9.9 Hz, H-1), 4.54 (dABq, 4H, J 1.3, 14.3 Hz, $CH_2Ar$), 4.10 (bd, 2H, J 2.6 Hz, H-4), 3.74 (dd, 4H, J 4.2, 11.5 Hz, H-6a), 3.73 (dd, 2H, J 9.4, 11.4 Hz, H-2), 3.61 (dd, 2H, J 4.7, 11.5 Hz, H-6$^b$), 3.50 (brdd, 2H, J 4.9, 6.1 Hz, H-5), 3.41 (dd, 2H, J 3.2, 9.2 Hz, H-3) 1.26 (s, 18H, tBu). HRMS calculated for $C_{40}H_{50}NaO_{14}S$ (M+Na)$^+$: 809.2819. found 809.2839.

Bis-{3-O-[(6-chloro-2H-1-benzopyran-2-on-3-yl)-methyl]-β-D-galactopyranosy}sulfane (27)

$^1$H NMR (DMSO-$d_6$, 400 MHz) δ: 8.20 (s, 2H, ArH), 7.78 (d, 2H, J 2.5 Hz, ArH), 7.64 (dd, 2H, J 2.5, 8.8, Hz, ArH), 7.48 (d, 2H, J 8.8 Hz, ArH), 5.21 (d, 2H, J 5.8 Hz, HO-2), 4.62 (m, 6H, H-1, HO-4, HO-6), 4.54 (dABq, 4H, J 1.3, 14.6 Hz, $CH_2Ar$), 4.03 (br s, 2H, H-4), 3.64-3.36 (m, 8H, H-2, H-3, H-5, H-6). HRMS calculated for $C_{32}H_{32}Cl_2NaO_{14}S$ (M+Na)$^+$: 765.0788. found 765.0807.

Bis-{3-O-[(6-fluoro-2H-1-benzopyran-2-on-3-yl)-methyl]-β-D-galactopyranosyl}sulfane (28)

$^1$H NMR (DMSO-$d_6$, 400 MHz) δ: 8.20 (brs, 2H, ArH), 7.50 (m, 6H, ArH), 7.64 (dd, 2H, J 2.5, 8.8, Hz, ArH), 7.48 (d, 2H, J 8.8 Hz, ArH), 5.21 (brs, 2H, HO-2), 4.60 (m, 10H, H-1, HO-4, HO-6, $CH_2Ar$), 4.03 (br s, 2H, H-4), 3.69-3.25 (m, 8H, H-2, H-3, H-5, H-6). HRMS calculated for $C_{32}H_{32}F_2NaO_{14}S$ (M+Na)$^+$: 733.1379. found 733.1411.

Bis-{3-O-[(6,7-difluoro-2H-1-benzopyran-2-on-3-yl)-methyl]-β-D-galactopyranosy}sulfane (29)

$^1$H NMR (DMSO-$d_6$, 400 MHz) δ: 8.17 (s, 2H, ArH), 7.80 (dd, 2H, J 8.8, 10.3 Hz, ArH), 7.73 (dd, 2H, J 6.8, 11.1 Hz, ArH), 4.60 (d, 2H, J 9.8 Hz, H-1), 4.53 (ABq, 4H, J 1.3, 14.9 Hz, $CH_2Ar$), 4.02 (br d, J 2.4 Hz, 2H, H-4), 3.62 (t, 2H, J 9.8

Hz, H-2), 3.54, 3.38 (2m, 8H, H-2, H-3, H-5, H-6). HRMS calculated for $C_{32}H_{30}F_4NaO_{14}S$ (M+Na)$^+$: 769.1190. found 769.1222.

Bis-{3-O-[(5-chloro-2H-1-benzopyran-2-on-3-yl)-methyl]-β-D-galactopyranosy}sulfane (30)

$^1$H NMR (DMSO-d$_6$, 400 MHz) δ: 8.41 (brs, 2H, ArH), 7.60 (brt, 2H, J 8.2 Hz, ArH), 7.51 (dd, 2H, J 1.1, 8.0, Hz, ArH), 7.44 (brd, 2H, J 8.2 Hz, ArH), 4.62 (d, 2H, J 9.7 Hz, H-1), 4.58 (dABq, 4H, J 1.7, 15.9 Hz, CH$_2$Ar), 4.05 (br d, 2H, J 2.7 Hz, H-4), 3.64 (t, 2H, J 9.4 Hz, H-2), 3.55 (dd, 2H, J 6.5, 11.5 Hz, H-6$^a$), 3.50 (dd, 2H, J 6.1, 11.5 Hz, H-6$^b$), 3.40 (dd, 2H, J 3.1, 9.2 Hz, H-3). HRMS calculated for $C_{32}H_{32}Cl_2NaO_{14}S$ (M+Na)$^+$: 765.0788. found 765.0793.

Bis-{3-O-[(5-fluoro-2H-1-benzopyran-2-on-3-yl)-methyl]-β-D-galactopyranosyl}sulfane (31)

$^1$H NMR (DMSO-d$_6$, 400 MHz) δ: 8.32 (brs, 2H, ArH), 7.62 (m, 2H, ArH), 7.27 (m, 4H, ArH), 5.31 (brs, 2H, HO-2), 4.61 (m, 10H, H-1, HO-4, HO-6, CH$_2$Ar), 4.03 (br s, 2H, H-4), 3.68-3.35 (m, 10H, H-2, H-3, H-5, H-6). HRMS calculated for $C_{32}H_{32}F_2NaO_{14}S$ (M+Na)$^+$: 733.1379. found 733.1407.

Bis-{3-O-[(5,6-difluoro-2H-1-benzopyran-2-on-3-yl)-methyl]-β-D-galactopyranosyl}sulfane (32)

$^1$H NMR (DMSO-d$_6$, 400 MHz) δ: 8.35 (brs, 2H, ArH), 7.70 (brq, 2H, J 5.4 Hz, ArH), 7.34 (brd, 4H, J 4.4 Hz, ArH), 5.35 (brd, 2H, J 5.6 Hz, HO-2), 4.61 (m, 10H, H-1, HO-4, HO-6, CH$_2$Ar), 4.04 (br s, 2H, H-4), 3.69-3.36 (m, 10H, H-2, H-3, H-5, H-6). HRMS calculated for $C_{32}H_{30}F_4NaO_{14}S$ (M+Na)$^+$: 769.1190. found 769.1220.

Bis-{3-O-[(6-trifluoromethoxy-2H-1-benzopyran-2-on-3-yl)-methyl]-β-D-galactopyranosy}sulfane (33)

$^1$H NMR (DMSO-d$_6$, 400 MHz) δ: 8.27 (brs, 2H, ArH), 7.73 (brs, 2H, ArH), 7.61 (brdd, 2H, J 2.3, 8.6 Hz, ArH), 7.57 (d, 2H, J 9.0 Hz, ArH), 5.21 (brs, 2H, HO-2), 4.62 (m, 4H, HO-4, HO-6), 4.62 (d, 2H, J 9.7 Hz, H-1), 4.56 (bABq, 4H, J 11.8 Hz, CH$_2$Ar), 4.04 (br s, 2H, H-4), 3.64-3.50 and 3.43-3.35 (2m, 10H, H-2, H-3, H-5, H-6). HRMS calculated for $C_{34}H_{32}F_6NaO_{16}S$ (M+Na)$^+$: 865.1213. found 865.1247.

Bis-{3-O-[(7-methyl-2H-1-benzopyran-2-on-3-yl)-methyl]-β-D-galactopyranosy}sulfane (34)

$^1$H NMR (DMSO-d$_6$, 400 MHz) δ: 8.20 (s, 2H, ArH), 7.56 (d, 2H, J7.9 Hz, ArH), 7.26 (s, 2H, ArH), 7.20 (brd, 2H, J 6.9 Hz, ArH), 4.61 (d, 2H, J 9.8 Hz, H-1), 4.53 (dABq, 4H, J 15.2 Hz, CH$_2$Ar), 4.03 (brs, 2H, H-4), 3.63 (t, 2H, J 9.4 Hz, H-2), 3.55 (m, 4H, H-6), 3.58-3.48 (dd, 2H, J 6.1, 11.5 Hz, H-6$^b$), 3.43-3.38 (m, 4H, H-3, H-5). HRMS calculated for $C_{34}H_{38}NaO_{14}S$ (M+Na)$^+$: 725.1880. found 725.1904.

Examples of In Vivo Efficacy of Galectin Inhibition in Fibrosis, Inflammation and Cancer Inflammation As mentioned above, many studies suggest a role for galectin-3 in enhancement of the inflammatory response. For example, the addition of galectin-3 to neutrophil leukocytes from an inflammatory site, or primed by exposure to LPS, results in increased generation of toxic oxygen radicals. Lactose can inhibit this response (Almquist et al., 2001). More recently, key important observations are that galectin-3 is rate-limiting in macrophage differentiation and myofibroblast activation (Mackinnon et al., 2008, Mackinnon et al., 2011), which in turn initiates fibrosis processes. Galectin-3 inhibition was in these models demonstrated to block macrophage differentiation and myofibroblast activation, and hence fibrosis, which indeed validated galectin-3 as a target for therapeutic intervention in inflammatory/fibrotic processes. The substances described in the present invention would be much more effective as inhibitors of the above mentioned responses than lactose because they are much more potent galectin-3 inhibitors. They would also be much more useful in vivo than lactose and the galectin-3C because they are small molecules, more hydrophobic and probably more stable to degradation.

Effect on Inflammatory Bowel Disease

The goal of the study is to demonstrate the ability of galectin-3 inhibitors of the present invention to reduce or eliminate inflammation and/or fibrosis in a model of intestinal inflammation.

Female 8-12-week-old CBA/J mice (Jackson Laboratories, Bar Harbor, Me.) receive 20 mg streptomycin in 0.1 M Hank's buffered salt solution (HBSS) to eradicate the commensal microbiota 24 hours prior to infection with 3 106 colony-forming units (cfu) *S. typhimurium* strain SL1344 in 100 k 0.1 M HEPES buffer (pH 8.0) by oral gavage. Control mice receive 100 k 0.1 M HEPES by oral gavage.

All groups are treated with 0.5 mg/ml levofloxacin beginning day 8, post-infection to allow time for the inflammation and fibrosis to develop but to eradicate the inflammatory response to *S. typhimurium*.

Mice from selected groups are treated with different doses of the galectin-3 inhibitors starting from either day 1, 8, 9, or 12 and continuing through to termination of the study. Dosing routes employed include oral, subcutaneous, intraperitoneal and i.v.

Animals are euthanized day 21 post *S. typhimurium* infection. Cecum and distal colon are dissected, measured, weighed, and photographed. Cecal and distal colon are snap-frozen in liquid nitrogen and stored at −80° C. for molecular analysis and both tissue sections are collected and preserved in formalin for histological analysis.

Sections are assayed for expression of fibrosis and inflammation markers, including TNF-alpha, IL-1, TGF-β, IL-12, IL-6, Galectin-3, IGF-1, and CTGF, using both RT-PCR, immunohistochemistry and ELISA techniques. Sections are inspected by an independent pathologists, and scored for degree of inflammation and fibrosis using a standardized scale.

Cancer

As mentioned above, several studies of models of human cancer in mice indicate that enhanced expression of galectin-3 results in faster tumor growth and more metastasis (reviewed by Leffler, 2001 and Takenaka et al in Leffler (editor), 2004b). Injection of a modified polysaccharide (citrus pectin) hypothesized to inhibit galectin-3, but perhaps also other proteins, was reported to diminish prostate cancer in rat (Pienta et al., 1995). A lactosylated steroid was demonstrated to have a therapeutic beneficial effect in lymphoma and glioblastoma models (Ingrassia et al., 2006). A lactusolyl-leucine derivative proposed to inhibit galectin-3 have been evidenced to enhance sensitivity of tumor cells to Taxol-induced apoptosis in vivo (Glinsky et al., 2009). Hence, potent small-molecule inhibitors of galectin-3 are expected to have similar anticancer effects as galectin-3C (John et al., 2003).

Model of Cancer

Groups of CD-1 nude mice are xenografted subcutaneously with a cells from a human tumour cell line. Treatments are initiated when tumor growth reached approximately 130 mm$^3$. Mice are divided into groups and treatments are administered at various frequencies and doses from this time and include vehicles and active control substances as well as galectin-3 inhibitors of the present invention. The tumor growths and body weight change are followed for 28 days.

Model of Lung Inflammation and Fibrosis

Female C57/B16 mice (10-14 weeks old) are anaesthetized with halothane, and bleomycin or saline is administered intratracheally (33 μg in 50 μl of saline) and lungs harvested on day 26. Different doses of one or more of the galectin-3 inhibitor(s) according to the invention is/are instilled into the lungs of mice on days 18, 20, 22 and 24 after the bleomycin induced lung injury. Fibrosis is assessed by histological score of collagen stained lung sections and by total collagen content by Sircol assay as described in MacKinnon et al. 2012.

Effect on Alveolar Epithelial Cells

Primary alveolar epithelial cells from WT mice are plated and treated with TGF-β1 in the presence or absence of the galectin-3 inhibitor. Cells are lysed and analyzed for active β-catenin, total β-catenin and β-actin by western blot.

Immunohistochemistry

Paraffin-embedded sections of mouse tissue are stained with Masson's trichrome and haemotoxylin and eosin (H&E) as per manufacturer's instructions. Sections are processed for immunohistochemistry and the following primary antibodies used: mouse anti-active (ABC) beta-catenin (Millipore) and sections visualized and quantified.

Determination of Lung Fibrosis and Inflammation

Histological lung inflammation and fibrosis score are carried out in Masson's trichrome stained sections. Inflammation (peribronchiolar, perivascular, and alveolar wall thickness) scored in >5 random fields at magnification ×630 using the following system (peribronchiolar and perivascular, 1=no cells, 2=<20 cells, 3=20–100 cells, 4=>100 cells; alveolar wall thickness, 1=no cells, 2=2–3 cells thick, 3=4–5 cells thick, 4=>5 cells thick). The combined inflammatory score is the sum of these scores. Fibrosis score is evaluated as the area of the section positively stained for collagen (1=none, 2=<10%, 3=<50%, 4=>50%). Only fields where the majority of the field is composed of alveoli are scored.

Determination of Lung Collagen by Sircol Assay

Collagen content in the left lung lobe is determined by sircol assay as per manufacturer's instructions. The left lobe is minced in 5 ml of 3 mg/ml pepsin in 0.5 M acetic acid and incubated with shaking at 4° C. for 24 h. Cleared lung extract (0.2 ml) is incubated with 0.8 ml sircol reagent for 1 h at room temperature and precipitated collagen centrifuged at 10,000 g for 5 min at 4° C. Pellets solubilised in 1 ml 1 M NaOH and absorbance measured at 570 nm alongside collagen standards.

Primary Type II Alveolar Epithelial Cell Isolation

Treated and control mouse type II lung alveolar epithelial cells (AECs) are extracted following a standard method. Briefly, 1 ml of 50 U/ml dispase (BD Biosciences) is administered intratracheally into perfused lungs followed by instillation of 0.5 ml of 1% low melting point agarose. The agarose within the upper airways is allowed to set on ice for 2 minutes and the lungs are placed in 4 ml 50 U/ml dispase for 45 min at room temperature. The lung lobes minus the upper airways are then dispersed in DMEM containing 50 μg/ml DNAse I (Sigma-Aldrich, UK). The cell suspension is passed through a 100-μm cell strainer and the cells washed in DMEM followed by resuspension in DMEM containing 10% FCS. The cell suspension is plated onto tissue culture plastic for 1 h to allow any contaminated fibroblasts and macrophages to adhere. Non-adherent epithelial cells are counted and cultured for 2 days on tissue culture plastic or cover-slips pre-coated with 5 μg/ml collagen (AMS Biotechnology) and 10 μg/ml fibronectin (Sigma-Aldrich), Cells are washed three times in PBS before treatment. Epithelial cells are either incubated in DMEM containing 10% FCS, 50 U/ml penicillin, 50 μg/ml streptomycin and 5 μg/ml L-glutamine or transferred to complete mouse media (DMEM/F-12 containing 0.25% BSA, 10 nM hydrocortisone, 5 μg/ml Insulin-Transferrin-Sodium-Selenite (ITS) and supplemented with 0.1 mg/ml sodium succinate, 75 μg/ml succinic acid and 1.8 μg/ml choline bitartrate).

Western Blotting

Cells are lysed in 25 mM HEPES pH 7.4, 0.3 M NaCl, 1.5 mM MgCl2, 0.2 mM EDTA, 0.5% triton X-100, 0.5 mM dithiothreitol, 1 mM sodium orthovanadate and protease inhibitors (Boehringer Mannheim, Sussex, UK; prepared as per manufacturers instructions). Lysates equilibrated for protein using Pierce BCA protein assay reagent (Pierce) and resolved on 12% SDS-PAGE gels. Western blot analysis undertaken using the following primary antibodies; rabbit anti beta-catenin, (BD Biosciences), rabbit polyclonal anti-beta-actin antibody (Sigma, UK), mouse anti-active (ABC) beta-catenin (Millipore).

Inhibition of Neovascularization

Vascular endothelial growth factor (VEGF) signaling though VEGF receptor-2 (VEGFR2) is the primary angiogenic pathway, of which galectin-1 and galectin-3 proteins are important modulators.

Neovascularization in the eye is induced in mouse corneas by cauterization using silver nitrate. A group of subjects are sub-conjunctivally injected every other day with one or more of the galectin-3 inhibitor(s) according to the invention in PBS containing 0.5% DMSO. Control subjects are sub-conjunctivally injected with vehicle only (PBS containing 0.5% DMSO only). Another group of subjects are administered eye drops of either 10 μl of vehicle alone or 50 μM galectin-3 inhibitor in vehicle once per day.

After five days of either sub-conjunctival injection treatment or eye drop treatment, subjects are sacrificed, and flat mounts of corneas are excised, photographed, and stained with anti-CD31 to visualize blood vessels.

The density of blood vessels covering the whole cornea is quantified by ImageJ and is analyzed with Student's t test.

REFERENCES

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. Infect. Immun. Vol. 69: 832-837.

Barondes, S. H., Cooper, D. N. W., Gitt, M. A., and Leffler, H. (1994). Galectins. Structure and function of a large family of animal lectins. J. Biol. Chem. 269:20807-20810.

Blois, S. M., Ilarregui, J. M., Tometten, M., Garcia, M., Orsal, A. S., Cordo-Russo, R., Toscano, M. A., Bianco, G. A., Kobelt, P., Handjiski, B., et al. (2007). A pivotal role for galectin-1 in fetomaternal tolerance. Nat Med 13: 1450-1457.

Chen, W.-S., Leffler H., Nilsson, U. J., Panjwani, N. (2012). Targeting Galectin-1 and Galectin-3 Attenuates VEGF-A-induced Angiogenesis; Mol. Biol. Cell (suppl), Abstract No. 2695.

Cumpstey, I., Carlsson, S., Leffler, H. and Nilsson, U. J. (2005) Synthesis of a phenyl thio-β-D-galactopyranoside library from 1,5-difluoro-2,4-dinitrobenzene: discovery of efficient and selective monosaccharide inhibitors of galectin-7. *Org. Biomol. Chem.* 3: 1922-1932.

Cumpstey, I., Sundin, A., Leffler, H. and Nilsson, U. J. (2005) $C_2$-Symmetrical thiodigalactoside bis-benzamido derivatives as high-affinity inhibitors of galectin-3: Efficient lectin inhibition through double arginine-arene interactions. *Angew. Chem. Int. Ed.* 44: 5110-5112.

Cumpstey, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. *Chem. Eur. J.* 14: 4233-4245.

Dam, T. K., and Brewer, C. F. (2008). Effects of clustered epitopes in multivalent ligand-receptor interactions. *Biochemistry* 47: 8470-8476.

Delacour, D., Greb, C., Koch, A., Salomonsson, E., Leffler, H., Le Bivic, A., and Jacob, R. (2007). Apical Sorting by Galectin-3-Dependent Glycoprotein Clustering. *Traffic* 8: 379-388.

Delaine, T., Cumpstey, I., Ingrassia, L., Le Mercier, M., Okechukwu, P., Leffler, H., Kiss, R., and Nilsson, U. J. (2008). Galectin-Inhibitory Thiodigalactoside Ester Derivatives Have Anti-Migratory Effects in Cultured Lung and Prostate Cancer Cells. *J Med Chem* 51; 8109-8114.

Garner, O. B., and Baum, L. G. (2008). Galectin-glycan lattices regulate cell-surface glycoprotein organization and signalling. *Biochem Soc Trans* 36: 1472-1477.

Giguere, D., Patnam, R., Bellefleur, M.-A., St.-Pierre, C., Sato, S., and Roy, R. (2006). Carbohydrate triazoles and isoxazoles as inhibitors of galectins-1 and -3. *Chem Commun:* 2379-2381.

Glinsky, G. V., Price, J. E., Glinsky, V. V., Mossine, V. V., Kiriakova, G., and Metcalf, J. B. (1996). *Cancer Res* 56: 5319-5324.

Glinsky, V. V., Kiriakova, G., Glinskii, O. V., Mossine, V. V., Mawhinney, T. P., Turk, J. R., Glinskii, A. B., Huxley, V. H., Price, J. E., and Glinsky, G. V. (2009). Synthetic Galectin-3 Inhibitor Increases Metastatic Cancer Cell Sensitivity to Taxol-Induced Apoptosis In Vitro and In Vivo. *Neoplasia* 11; 901-909.

Huflejt, M. E. and Leffler, H. (2004) Galectin-4 in normal tissues and cancer. *Glycoconj. J.* 20: 247-255.

Ingrassia et al. (2006) A Lactosylated Steroid Contributes in Vivo Therapeutic Benefits in Experimental Models of Mouse Lymphoma and Human Glioblastoma. *J. Med. CHem.* 49: 1800-1807.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast *Cancer. Clin. Cancer Res.* 9: 2374-2383.

Lau, K. S., and Dennis, J. W. (2008). N-Glycans in cancer progression. *Glycobiology* 18: 750-760.

Lau, K. S., Partridge, E. A., Grigorian, A., Silvescu, C. I., Reinhold, V. N., Demetriou, M., and Dennis, J. W. (2007). Complex N-glycan number and degree of branching cooperate to regulate cell proliferation and differentiation. *Cell* 129: 123-134.

Leffler, H. and Barondes, S. H. (1986) Specificity of binding of three soluble rat lung lectins to substituted and unsubstituted mammalian beta-galactosides. *J. Biol. Chem.* 261: 10119-10126.

Leffler, H. Galectins Structure and Function—A Synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. *Glycoconj. J.* 19: 433-440.

Leffler, H., editor, (2004b) Special Issue on Galectins. *Glycoconj. J.* 19: 433-638.

Lin, C.-I., Whang, E. E., Donner, D. B., Jiang, X., Price, B. D., Carothers, A. M., Delaine, T., Leffler, H., Nilsson, U. J., Nose, V., et al. (2009). Galectin-3 Targeted Therapy with a Small Molecule Inhibitor Activates Apoptosis and Enhances Both Chemosensitivity and Radiosensitivity in Papillary Thyroid Cancer. *Mol Cancer Res* 7: 1655-1662.

MacKinnon, A. C., Farnworth, S. L., Henderson, N. C., Hodkinson, P. S., Kipari, T., Leffler, H., Nilsson, U. J., Haslett, C., Hughes, J., and Sethi T. (2008). Regulation of alternative macrophage activation by Galectin-3. *J. Immun.* 180; 2650-2658.

Mackinnon, A., Gibbons, M., Farnworth, S., Leffler, H., Nilsson, U. J., Delaine, T., Simpson, A., Forbes, S., Hirani, N., Gauldie, J., and Sethi T. (2012). Regulation of TGF-β1 driven lung fibrosis by Galectin-3. *Am. J. Resp. Crit. Care Med.*, in press.

Massa, S. M., Cooper, D. N. W., Leffler, H., Barondes, S. H. (1993) L-29, an endogenous lectin, binds to glycoconjugate ligands with positive cooperativity. *Biochemistry* 32: 260-267.

Partridge, E. A., Le Roy, C., Di Guglielmo, G. M., Pawling, J., Cheung, P., Granovsky, M., Nabi, I. R., Wrana, J. L., and Dennis, J. W. (2004). Regulation of cytokine receptors by Golgi N-glycan processing and endocytosis. *Science* 306: 120-124.

Perone, M. J., Bertera, S., Shufesky, W. J., Divito, S. J., Montecalvo, A., Mathers, A. R., Larregina, A. T., Pang, M., Seth, N., Wucherpfennig, K. W., et al. (2009). Suppression of autoimmune diabetes by soluble galectin-1. *J Immunol* 182: 2641-2653.

Pienta, K. J., Naik, H., Akhtar, A., Yamazaki, K., Replogle, T. S., Lehr, J., Donat, T. L., Tait, L., Hogan, V., and Raz, A. (1995). Inhibition of spontaneous metastasis in a rat prostate cancer model by oral administration of modified citrus pectin. *J Natl Cancer Inst* 87, 348-353.

Saegusa, J., Hsu, D. K., Chen, H. Y., Yu, L., Fermin, A., Fung, M. A., and Liu, F. T. (2009). Galectin-3 is critical for the development of the allergic inflammatory response in a mouse model of atopic dermatitis. *Am J Pathol* 174: 922-931.

Salameh, B. A., Leffler, H. and Nilsson, U. J. (2005) *Bioorg. Med. Chem. Lett.* 15: 3344-3346.

Salameh, B. A., Cumpstey, I., Sundin, A., Leffler, H., and Nilsson, U. J. (2010). 1H-1,2,3-Triazol-1-yl thiodigalactoside derivatives as high affinity galectin-3 inhibitors. *Bioorg Med Chem* 18: 5367-5378.

Salomonsson, E., Larumbe, A., Tejler, J., Tullberg, E., Rydberg, H., Sundin, A., Khabut, A., Frejd, T., Lobsanov, Y. D., Rini, J. M., Nilsson, U. J., and Leffler, H (2010). Monovalent interactions of galectin-1. *Biochemistry* 49: 9518-9532.

Sörme, P., Qian, Y., Nyholm, P.-G., Leffler, H., Nilsson, U. J. (2002) Low micromolar inhibitors of galectin-3 based on 3'-derivatization of N-acetyllactosamine. *ChemBioChem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., Magnusson, B.-G., Leffler H., and Nilsson, U. J. (2003b) Design and synthesis of galectin inhibitors. *Meth. Enzymol.* 363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* 334: 36-47.

Thijssen, V. L., Poirer, F., Baum, L. G., and Griffioen, A. W. (2007). Galectins in the tumor endothelium: opportunities for combined cancer therapy. *Blood* 110: 2819-2827.

Toscano, M. A., Bianco, G. A., Ilarregui, J. M., Croci, D. O., Correale, J., Hernandez, J. D., Zwirner, N. W., Poirier, F., Riley, E. M., Baum, L. G., et al. (2007). Differential glycosylation of TH1, TH2 and TH-17 effector cells selectively regulates susceptibility to cell death. *Nat Immunol* 8: 825-834.

The invention claimed is:

1. A compound of the general formula (I):

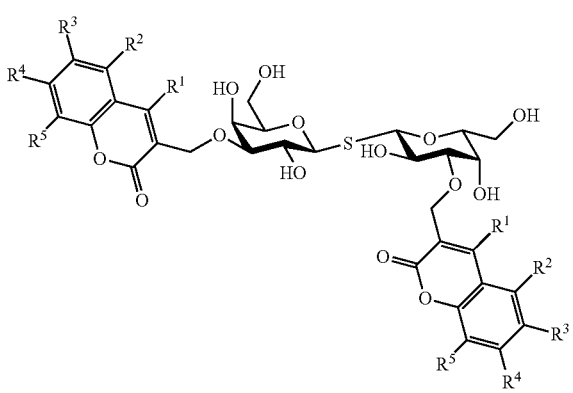

(I)

wherein:
$R^1$, $R^2$, $R^3$, $R^4$ and $R^5$ are independently selected from the group consisting of hydrogen, optionally substituted alkyl groups, halogens, optionally substituted alkoxy groups, hydroxyl group, substituted carbonyl groups, optionally substituted acyloxy groups, and optionally substituted amino groups, or wherein two, three, four or five of $R^1$, $R^2$, $R^3$, $R^4$ and $R^5$ in adjacent positions may be linked to form one or more rings, wherein the remaining of $R^1$, $R^2$, $R^3$, $R^4$ and $R^5$ is/are independently selected from the above group.

2. A compound according to claim 1, wherein $R^5$ is hydrogen.

3. A compound according to claim 1, wherein one of $R^2$ and $R^3$ is fluoro, the one of $R^2$ and $R^3$ that is not fluoro is hydrogen and $R^1$, $R^4$ and $R^5$ all are hydrogen.

4. A compound according to claim 1, wherein one of $R^3$ and $R^4$ is a hydroxyl group, the one of $R^3$ and $R^4$ that is not a hydroxyl group is hydrogen and $R^1$, $R^2$, and $R^5$ all are hydrogen.

5. A compound according to claim 1, wherein $R^2$ and $R^3$ are fluoro, and $R^1$, $R^4$ and $R^5$ all are hydrogen, or wherein $R^3$ and $R^4$ are fluoro, and $R^1$, $R^2$ and $R^5$ all are hydrogen.

6. A compound according to claim 1, wherein $R^2$ is chloro and $R^1$, $R^3$, $R^4$, and $R^5$ all are hydrogen.

7. A compound according to claim 1, wherein $R^2$ and $R^3$ are linked to form a benzene ring and $R^1$, $R^4$ and $R^5$ all are hydrogen.

8. A compound according to claim 1, wherein $R^1$, $R^2$, $R^3$, $R^4$ and $R^5$ all are hydrogen.

9. A compound according to claim 1, wherein said compound is selected from the group consisting of:
bis-{3-O-[(2H-1-benzopyran-2-on-3-yl)-methyl]-β-D-galactopyranosyl}sulfane,
bis-{3-O-[(7-chloro-2H-1-benzopyran-2-on-3-yl)-methyl]-β-D-galactopyranosyl}sulfane,
bis-{3-[(7-methoxy-2H-1-benzopyran-2-on-3-yl)-methyl]-β-D-galactopyranosyl}sulfane,
bis-{3-[(7-hydroxy-2H-1-benzopyran-2-on-3-yl)-methyl]-β-D-galactopyranosyl}sulfane,
bis-{3-[(6-hydroxy-2H-1-benzopyran-2-on-3-yl)-methyl]-β-D-galactopyranosyl}sulfane,
bis-{3-[(3H-naphtho[2,1-b]pyran-3-on-2-yl)-methyl]-β-D-galactopyranosyl}sulfane,
bis-{3-[(6-tert-butyl-2H-1-benzopyran-2-on-3-yl)-methyl]-β-D-galactopyranosyl}sulfane,
bis-{3-[(6-chloro-2H-1-benzopyran-2-on-3-yl)-methyl]-β-D-galactopyranosyl}sulfane,
bis-{3-[(6-fluoro-2H-1-benzopyran-2-on-3-yl)-methyl]-β-D-galactopyranosyl}sulfane,
bis-{3-[(6,7-difluoro-2H-1-benzopyran-2-on-3-yl)-methyl]-β-D-galactopyranosyl}sulfane,
bis-{3-[(5-chloro-2H-1-benzopyran-2-on-3-yl)-methyl]-β-D-galactopyranosyl}sulfane,
bis-{3-[(5-fluoro-2H-1-benzopyran-2-on-3-yl)-methyl]-β-D-galactopyranosyl}sulfane,
bis-{3-[(5,6-difluoro-2H-1-benzopyran-2-on-3-yl)-methyl]-β-D-galactopyranosyl}sulfane,
bis-{3-[(6-trifluoromethoxy-2H-1-benzopyran-2-on-3-yl)-methyl]-β-D-galactopyranosyl}sulfane,
bis-{3-[(7-methyl-2H-1-benzopyran-2-on-3-yl)-methyl]-β-D-galactopyranosyl}sulfane,
bis-{3-[(2H-1-benzopyran-2-on-3-yl)-methyl]-β-D-galactopyranosyl}sulfane,
bis-{3-[(7-hydroxy-2H-1-benzopyran-2-on-3-yl)-methyl]-β-D-galactopyranosyl}sulfane,
bis-{3-[(6-hydroxy-2H-1-benzopyran-2-on-3-yl)-methyl]-β-D-galactopyranosyl}sulfane,
bis-{3-[(6-fluoro-2H-1-benzopyran-2-on-3-yl)-methyl]-β-D-galactopyranosyl}sulfane,
bis-{3-[(6,7-difluoro-2H-1-benzopyran-2-on-3-yl)-methyl]-β-D-galactopyranosyl}sulfane,
bis-{3-[(5-chloro-2H-1-benzopyran-2-on-3-yl)-methyl]-β-D-galactopyranosyl}sulfane,
bis-{3-[(5-fluoro-2H-1-benzopyran-2-on-3-yl)-methyl]-β-D-galactopyranosyl}sulfane, and
bis-{3-[(5,6-difluoro-2H-1-benzopyran-2-on-3-yl)-methyl]-β-D-galactopyranosyl}sulfane,
bis-{3-[(6-fluoro-2H-1-benzopyran-2-on-3-yl)-methyl]-β-D-galactopyranosyl}sulfane,
bis-{3-[(6,7-difluoro-2H-1-benzopyran-2-on-3-yl)-methyl]-β-D-galactopyranosyl}sulfane,
bis-{3-[(5-chloro-2H-1-benzopyran-2-on-3-yl)-methyl]-β-D-galactopyranosyl}sulfane,
bis-{3-[(5-fluoro-2H-1-benzopyran-2-on-3-yl)-methyl]-β-D-galactopyranosyl}sulfane, and
bis-{3-[(5,6-difluoro-2H-1-benzopyran-2-on-3-yl)-methyl]-β-D-galactopyranosyl}sulfane.

10. A compound according to claim 1, wherein said compound is bis-{3-[(5,6-difluoro-2H-1-benzopyran-2-on-3-yl)-methyl]-β-D-galactopyranosyl}sulfane.

11. A composition comprising a compound according to claim 1 and a pharmaceutically acceptable adjuvant, diluent, excipient and/or carrier.

12. A composition comprising from 1 to 99 weight % of a pharmaceutically acceptable adjuvant, diluent, excipient and/or carrier and from 1 to 99 weight % of a compound according to claim 1.

13. A method for treatment of a disorder relating to the binding of a galectin to a ligand in a mammal, wherein said disorder is selected from the group consisting of inflammation, fibrosis, septic shock, cancer, autoimmune diseases, metabolic disorders, heart disease, heart failure, pathological angiogenesis, and eye diseases comprising adminstering an amount of at least one compound according to claim 1 to said mammal in need of said treatment effective to treat said disorder.

14. The method of claim 13, wherein said galectin is galectin-3.

15. The method of claim 13, wherein said disorder is fibrosis and the fibrosis is selected from the group consisting of pulmonary fibrosis, liver fibrosis, kidney fibrosis, ophtalmological fibrosis and fibrosis of the heart.

16. The method of claim 13, wherein said disorder is pathological angiogenesis and the pathological angiogenesis is ocular angiogenesis or a disease or condition associated with ocular angiogenesis.

17. The method of claim 13, wherein said disorder is an eye disease and the eye diseases arediseaseis selected from age-related macular degeneration and corneal neovascularization.

18. The method of 13, wherein said disorder is cancer.

19. The method of 13, wherein said disorder is pathological angiogenesis and the pathological angiogenesis is neovascularization related to cancer.

* * * * *